US011322263B2

(12) United States Patent
Barkol et al.

(10) Patent No.: US 11,322,263 B2
(45) Date of Patent: May 3, 2022

(54) SYSTEMS AND METHODS FOR COLLABORATIVE NOTIFICATIONS

(71) Applicant: GE Precision Healthcare LLC, Milwaukee, WI (US)

(72) Inventors: Omer Barkol, Haifa (IL); Ludovic Avot, Croissy sur Seine (FR); Andreas Tzanetakis, Madison, WI (US); David Maddox Utt, Milwaukee, WI (US); Michelle Townshend, Traverse City, MI (US)

(73) Assignee: GE Precision Healthcare LLC, Milwaukee, WI (US)

( * ) Notice: Subject to any disclaimer, the term of this patent is extended or adjusted under 35 U.S.C. 154(b) by 213 days.

(21) Appl. No.: 16/384,714

(22) Filed: Apr. 15, 2019

(65) Prior Publication Data

US 2020/0327996 A1    Oct. 15, 2020

(51) Int. Cl.
*G16H 80/00*    (2018.01)
*G16H 40/67*    (2018.01)

(52) U.S. Cl.
CPC ............. *G16H 80/00* (2018.01); *G16H 40/67* (2018.01)

(58) Field of Classification Search
CPC ........ G16H 40/67; G16H 10/20; G16H 10/60; G16H 15/00; G16H 80/00
See application file for complete search history.

(56) References Cited

U.S. PATENT DOCUMENTS

| | | |
|---|---|---|
| 9,536,049 B2 | 1/2017 | Brown et al. |
| 2014/0249830 A1 | 9/2014 | Gallopyn et al. |
| 2016/0371441 A1 | 12/2016 | Day et al. |
| 2017/0039336 A1 | 2/2017 | Bitran et al. |
| 2017/0140105 A1* | 5/2017 | Smith ................. G16H 10/40 |
| 2017/0181645 A1* | 6/2017 | Mahalingam ...... A61B 5/14532 |
| 2017/0235912 A1* | 8/2017 | Moturu ................. G16H 50/50 705/2 |
| 2019/0189293 A1* | 6/2019 | Tse ....................... G16H 20/10 |

* cited by examiner

*Primary Examiner* — Maroun P Kanaan
(74) *Attorney, Agent, or Firm* — McCoy Russell LLP

(57) ABSTRACT

Systems and methods are provided for presenting aggregate data in response to a natural language user input. In one example, a system includes a display and a computing device coupled to the display and storing instructions executable to output, to the display, a patient-specific communication thread including communication among one or more care providers monitoring a patient and a virtual healthcare assistant, generate, with the virtual healthcare assistant, a notification indicating a change in a state of the patient, and output, to the display, the notification, where the notification is displayable as part of the communication thread.

19 Claims, 17 Drawing Sheets

SYSTEMS AND METHODS FOR COLLABORATIVE NOTIFICATIONS

FIELD

Embodiments of the subject matter disclosed herein relate to a user interface for collaborative notifications and timelines.

BACKGROUND

Acute care of patients in a hospital or other medical facility may be carried out with multiple care providers per patient and may include multiple patient monitoring devices monitoring each patient. Thus, to ensure a rapid response should a patient's condition deteriorate, near-continuous monitoring of the output from the multiple monitoring devices may be necessary. Further, coordination of patient care among all the care providers may be complicated or time-consuming, further stretching care provider resources. Additionally, the presentation of patient medical information to the care providers may require multiple time-consuming and cumbersome requests or searches for information.

BRIEF DESCRIPTION

In one embodiment, a system includes a display and a computing device coupled to the display and storing instructions executable to output, to the display, a patient-specific communication thread including communication among one or more care providers monitoring a patient and a virtual healthcare assistant, generate, with the virtual healthcare assistant, a notification indicating a change in a state of the patient, and output, to the display, the notification, where the notification is displayable as part of the communication thread.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

Figure 1:
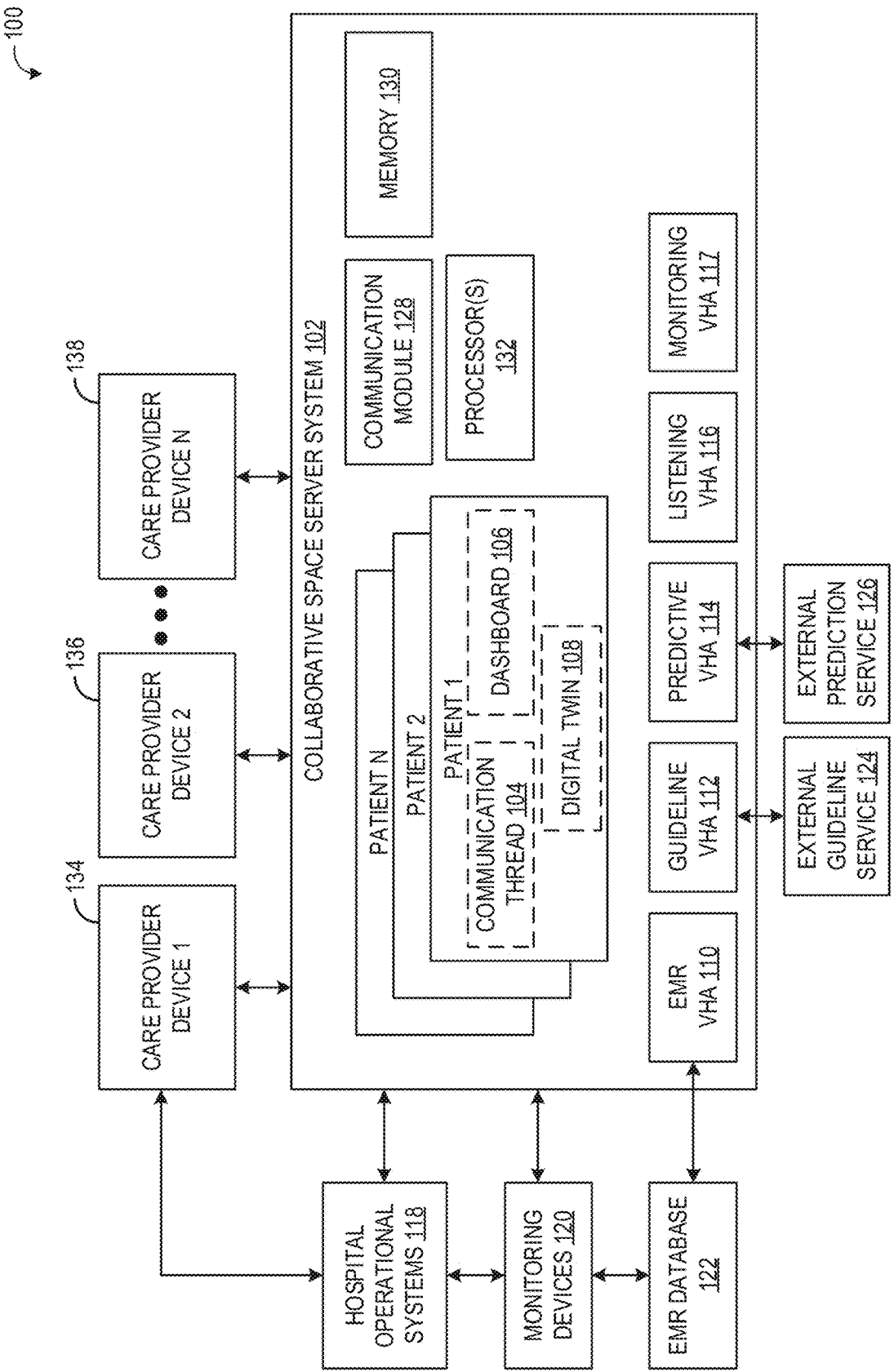
FIG. 1 schematically shows an example collaborative healthcare system.

The following description relates to various embodiments of a collaborative healthcare system that facilitates communication among care providers of a patient (which may be collectively referred to as a care provider team) and also utilizes machine and/or other deep learning models (e.g., in the form of virtual healthcare assistants) to perform certain patient monitoring and diagnostic activities. The collaborative healthcare system includes patient-specific communication channels that include communication thread-dashboard pairs to facilitate communication among the care providers and virtual healthcare assistants (also referred to as bots) on the communication thread while also graphically providing relevant patient care information (current vital signs, trends, medical history, etc.) to the care providers via the dashboard and/or communication thread.

The virtual healthcare assistants may function as information retrievers, data monitors, predictors, and more to assist the care providers. The virtual healthcare assistants may provide requested patient data (e.g., fetch data from an electronic medical record), detect changes in patient state and alert the care providers of the changed state (e.g., by detecting that a patient vital sign has reached a condition relative to a threshold), and provide care guidelines, suggested diagnostic tests, and diagnoses to the care providers. The virtual healthcare assistants may be trained to communicate using natural language including medical language, thereby allowing for care providers to communicate with the virtual healthcare assistants in the same manner as other care providers.

Each communication channel may be specific to a given patient in a given acute care facility or other medical facility or healthcare setting (e.g., hospital, urgent care facility, or nursing home). A communication channel may be initiated upon admission of the patient to the medical facility. Each care provider of the patient may be joined to the communication channel, thereby allowing collaboration and communication among all care providers (e.g., doctors, nurses, and/or specialists such as radiologists) of the patient. The one or more virtual healthcare assistants may also be joined to the communication channel. Communication occurring on the communication channel may be in the form of text messages, rich media, and/or other forms, thereby allowing care providers to view graphs of patient medical trends, medical images, and so forth. Messages sent and received on the communication channel may be saved at a central location as a communication thread, allowing care providers to access prior conversations on the channel. For example, if a virtual healthcare assistant detects a change in a patient condition that indicates potential health issues, such as high blood pressure, the virtual healthcare assistant may note the high blood pressure and alert the care provider(s) via the communication thread. The blood pressure may be displayed via the patient dashboard along with the alert. A care provider may view the blood pressure measurement by selecting the alert in the communication thread. Later, the care provider may select a graphical display of the alert in the dashboard in order to launch the portion of the communication thread in which the blood pressure alert was issued.

The dashboard and communication thread may be viewable from a variety of client devices, including but not limited to a provider client device (such as a monitor in a nurse's station) and a provider mobile device (such as a tablet or smart phone). Thus, care providers may have access to relevant data and assistance from the virtual healthcare assistants from virtually any allowed location within the medical facility, and even off-site locations in some examples.

Further, the collaborative healthcare system described herein may facilitate management and presentation of patient-specific notifications and care timelines. For example, via the collaborative healthcare system, notifications are possible for different reasons. One important type of notification is when a patient deteriorates. Other notifications can be triggered due to an event that occurred and was requested to be notified, some other care-team member requires the specific attention of a caregiver, and more.

Thus, according to embodiments disclosed herein, the collaborative healthcare system is configured to to allow its users—the care-team—to utilize notifications to assist the prevention of patient deterioration in a way that is personalized for the caregiver and for the patient, act on the notification immediately, and while minimizing alarm fatigue. Notifications may come in three different levels—low, medium, and high—which have different settings for when the notifications appear and whether one should actively act on the notification or not. For example, once a notification is displayed on a caregiver device and accepted (e.g., selected) by the caregiver, the caregiver may act on it in different manners, including dismissing or snoozing the notification. One other option is to "go to patient"—this will take the caregiver directly to the patient's communication channel—whether the caregiver is in the application or out of it. These options may be supported for all notification levels but may be required for high level notifications The level of notification per notification type may be set either on the organization level (e.g., hospital administrator level) or on a caregiver level. Moreover, the organization may set default levels that are set per caregiver roles or titles. These settings may be adjustable by the caregiver or set as non-adjustable. An example of how different roles may be set differently for different caregiver roles includes a surgeon, who has hundreds of patients, setting notifications only when he or she is directly mentioned in a communication thread. One the other hand, a nurse in charge might adjust settings to receive notifications for new patients in a ward while all other caregivers might not want to receive a notification each time a new patient is admitted to the ward.

The notifications may be displayed on one or more devices used by the caregiver(s). For example, once output for display, a notification may pop up on a display screen of a caregiver device, regardless of what application(s) are currently executing on the device. Once a notification is generated and/or output for display, the notification may also be registered (e.g., saved) in the communication channel for the patient. For example, the notification may be manifested as a banner within the patient communication thread. The banners may be added in to the communication thread at the relevant time and therefore will present as part of the communication thread chronological flow. In addition, notifications may be added to a patient timeline that is part of the patient's communication thread, which will be explained in more detail below.

In some examples, a caregiver may request (e.g., to a virtual healthcare assistant) in a simple way using natural language that a personalized notification be generated, that may be aimed for a specific patient. Such a notification may be triggered by a request as simple as "remind me to take vitals in 15 minutes." Such patient specific notifications may be more evolved and depend on clinical data of the patient. As an example, a caregiver may request "let me know if the systolic blood pressure goes below 100."

In this way, notifications may be generated upon caregiver request and/or automatically. When a notification is received, a caregiver may be able to act on the notification, including going directly to a patient's communication channel from the notification. The notifications may be set by default to match the role of a caregiver. The notifications may also be manifested in a patient specific manner in a communication channel as part of the communication thread and timeline for the patient and so are not volatile, which may increase the likelihood a caregiver will view and act on a notification. Notifications may be triggered in a personal manner (both for the patient and by a caregiver) and in a natural language manner, which may increase caregiver interaction with the notifications.

In another example, a care provider may request to view a timeline of a patient, which may include relevant/important patient medical events/information that occurred or was documented during a predefined time period, such as a time period that corresponds to a shift at the medical facility (e.g., 8 or 12 hours). A communication channel for a patient may include a communication thread where the care team for the patient may collaborate and interact with one or more virtual healthcare assistants. The communication channel may include additional tabs that may be selected by a caregiver in order to view the main aspects that the caregiver may need when reviewing the patient status either far from the patient or at the bedside, including aspects such as the latest vitals, lab results, and main relevant notes. Still, to review the latest events of a patient, e.g., to facilitate handover between shifts, a caregiver may desire to have a way to visualize these events. Thus, the timeline (as described herein) may allow a caregiver to create a summary of the events that happened during a shift, where the timeline includes different messages, notifications, and patient medical data, which may be useful for shift handovers. A timeline may include medium- and high-level notifications, any message in the communication thread (that was either sent by a virtual healthcare assistant or by one of the care team members) that was chosen to be included in the timeline, and/or patient medical data and graphs. Choosing a message to be included in the timeline may be done by any one of the care team members. The timeline then presents a single view of the patient's status in the last shift (e.g., the prior 8, 12, or 24 hours).

Figure 2:
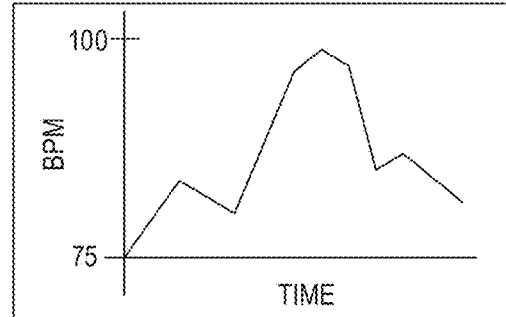
FIG. 2 shows an example display device displaying a communication thread occurring on a communication channel of the collaborative healthcare system.
Figure 3:
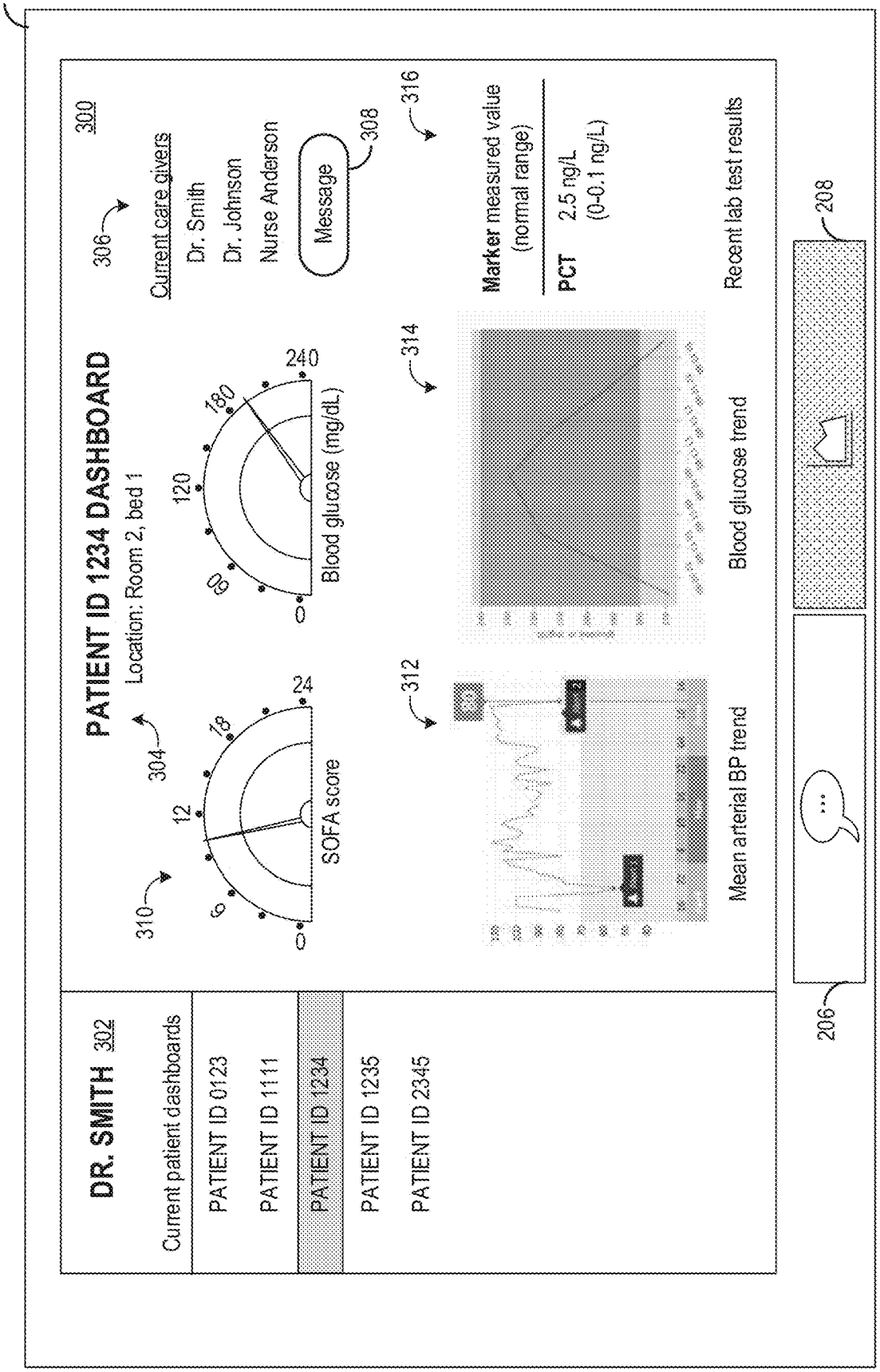
FIG. 3 shows an example display device displaying a dashboard of the collaborative healthcare system.
Figure 4:
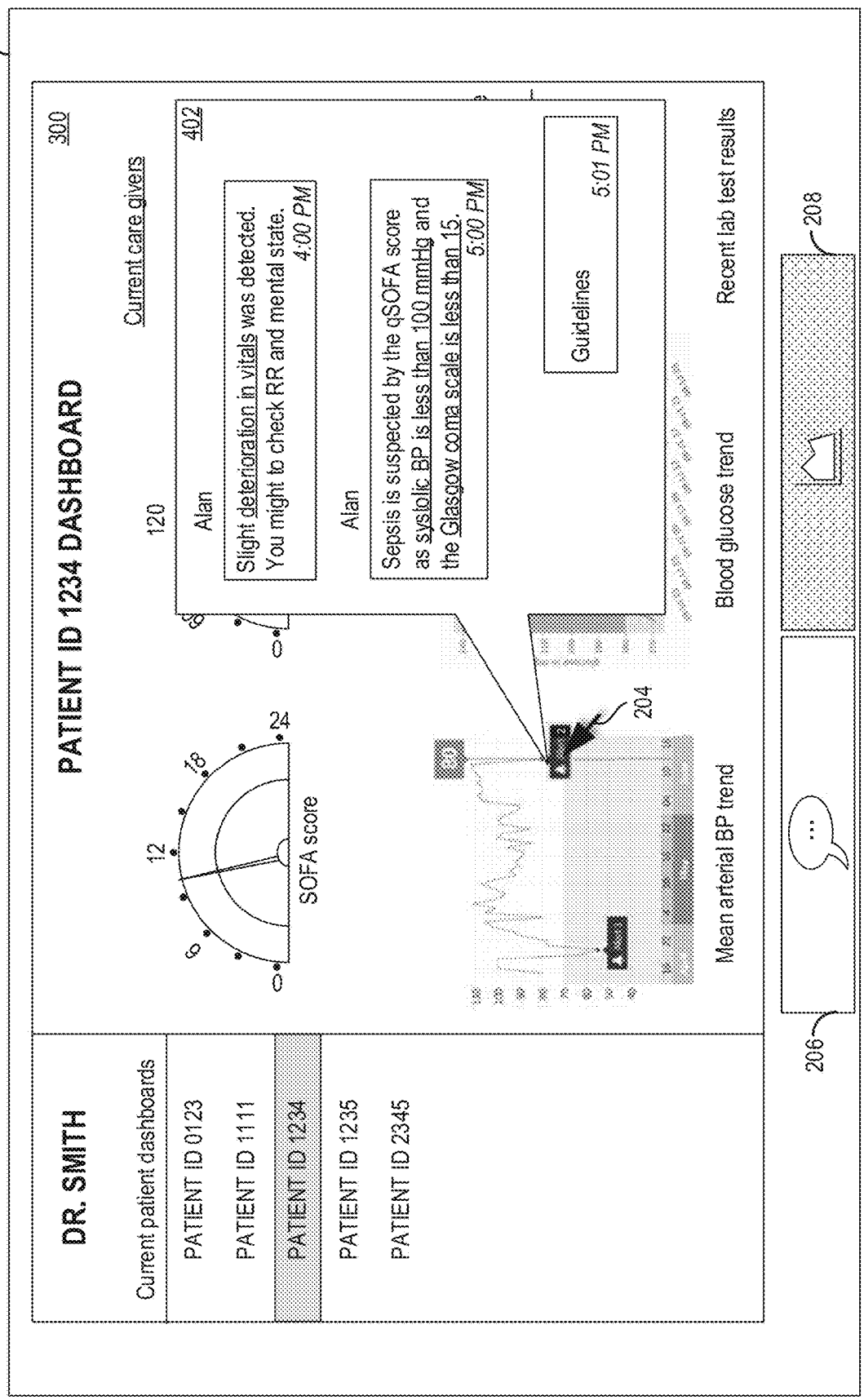
FIG. 4 shows an example display device displaying the dashboard of FIG. 3 including display of a portion of the communication thread of FIG. 2.
Figure 5:
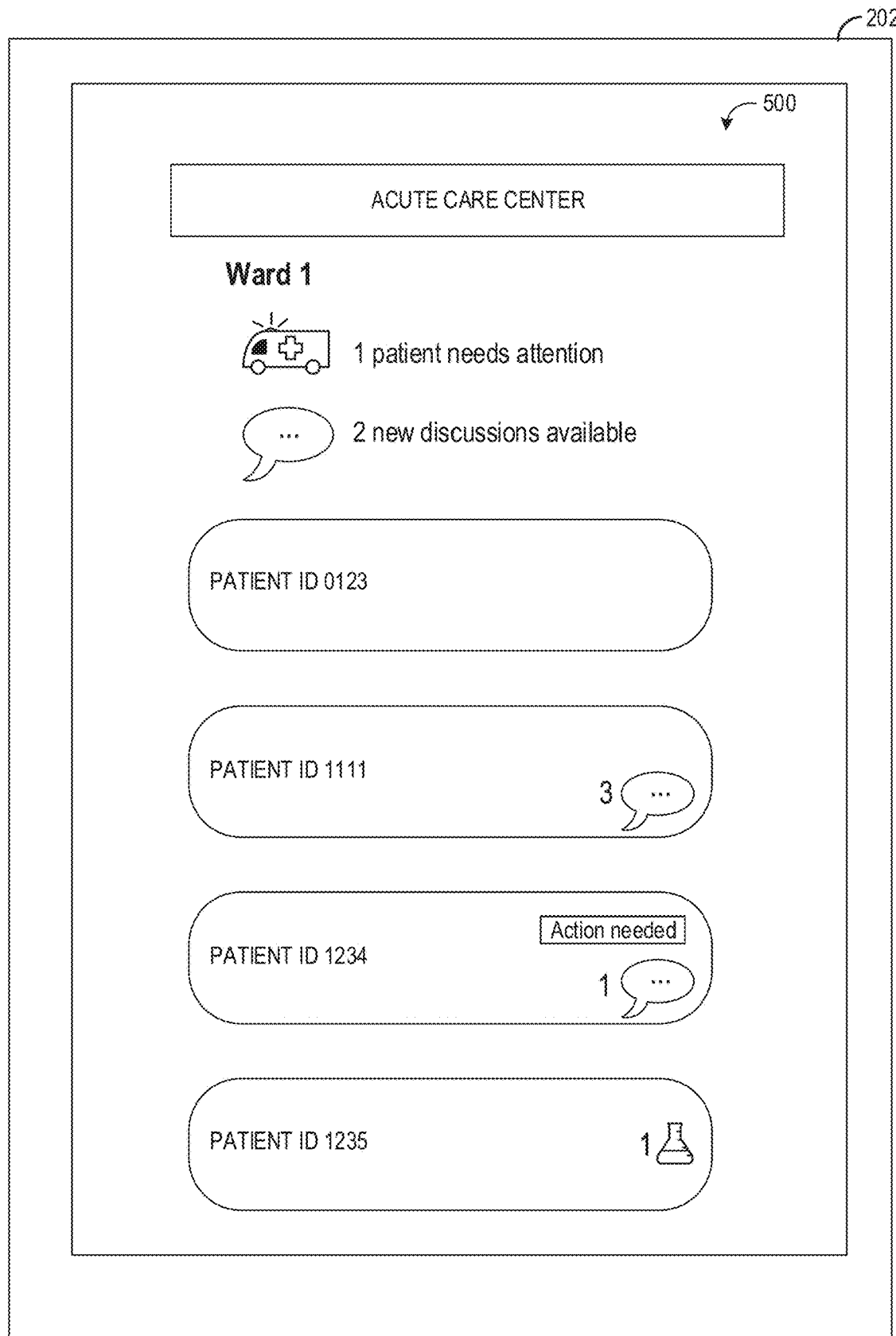
FIG. 5 shows an example display device displaying a collaborative interface.
Figure 6:
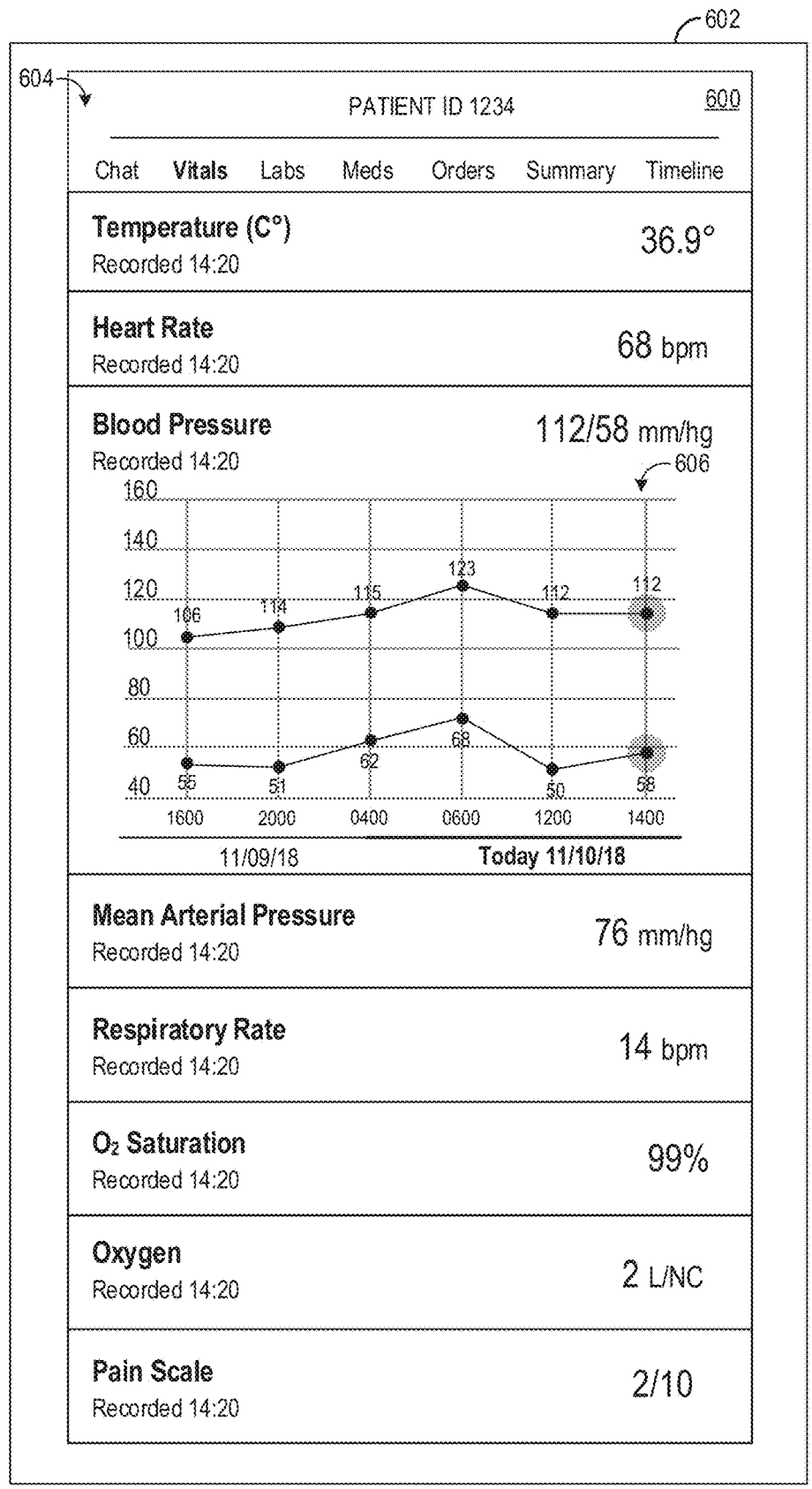
FIG. 6 shows an example display device displaying another example dashboard of the collaborative healthcare system.
Figure 7:
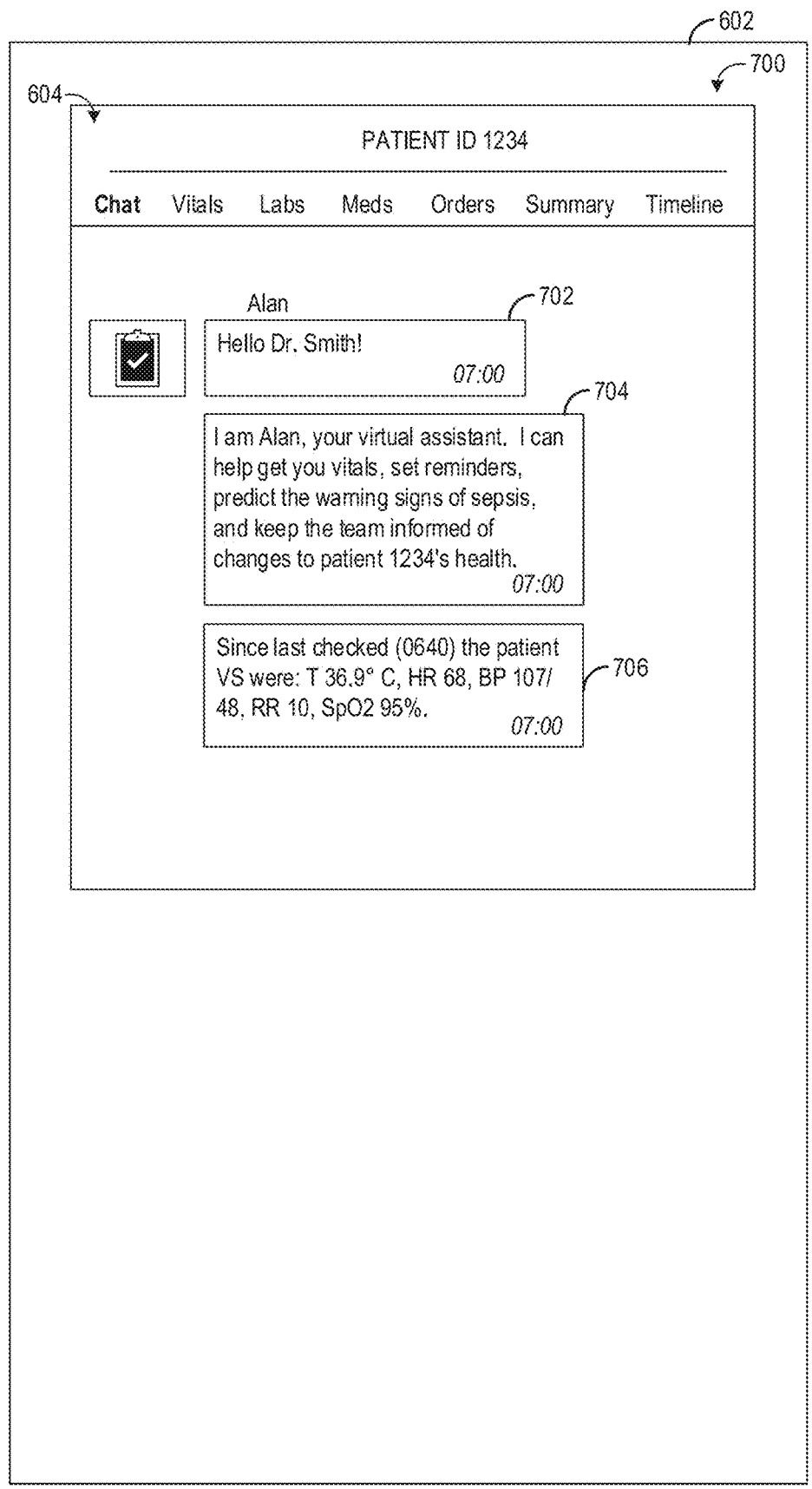
FIG. 7 shows an example display device displaying an example communication thread occurring on a communication channel of the collaborative healthcare system.
Figure 8A:
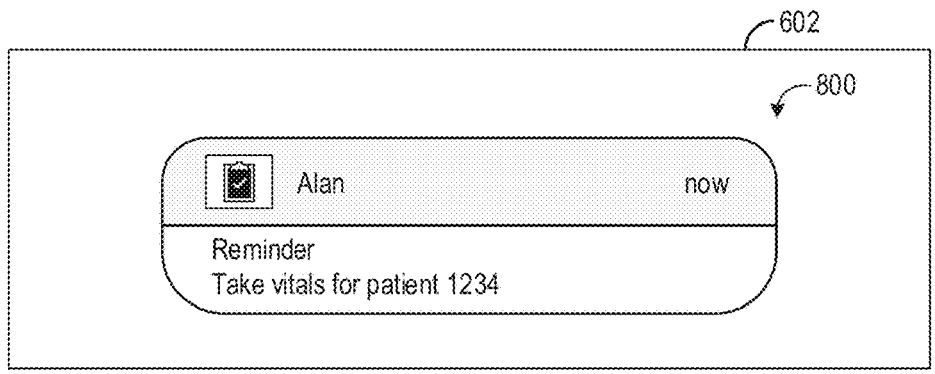
FIGS. 8A-8C show an example display device displaying example notifications that may be output via a communication channel of the collaborative healthcare system.
Figure 8B:
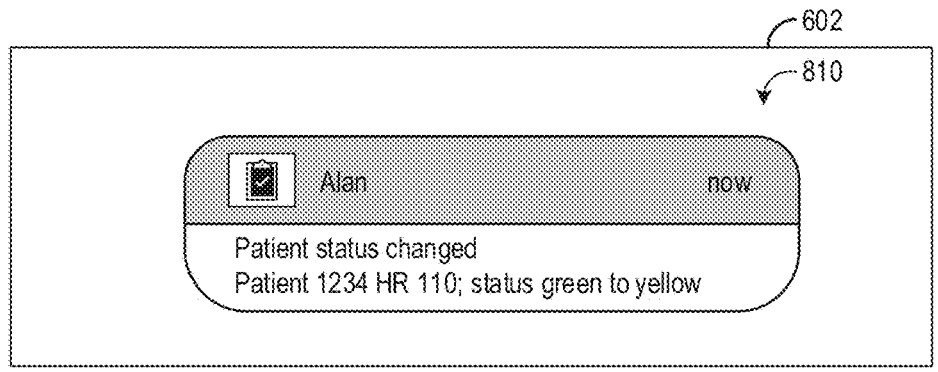
Figure 8C:
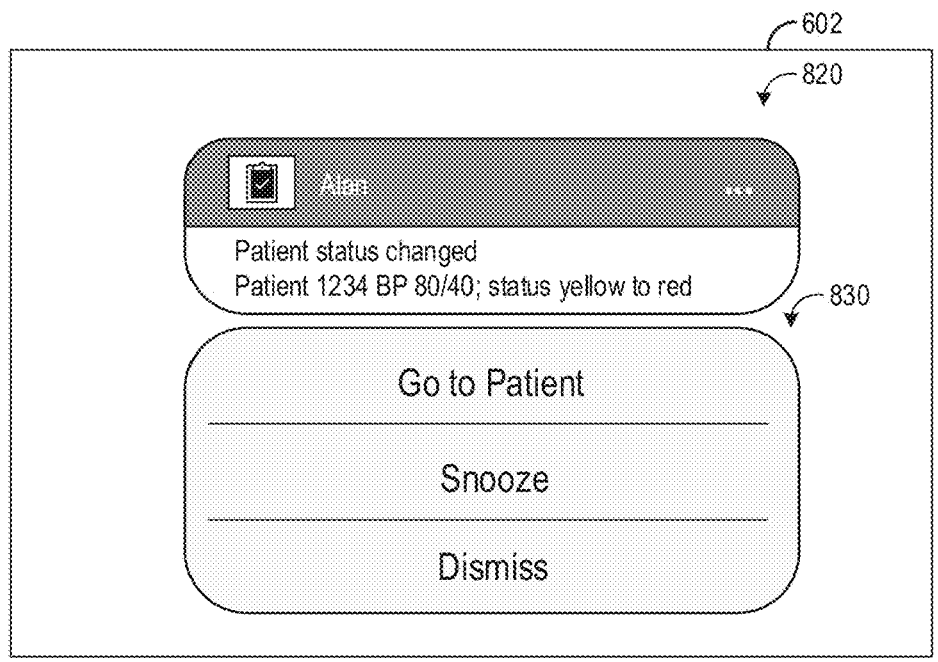
Figure 9:
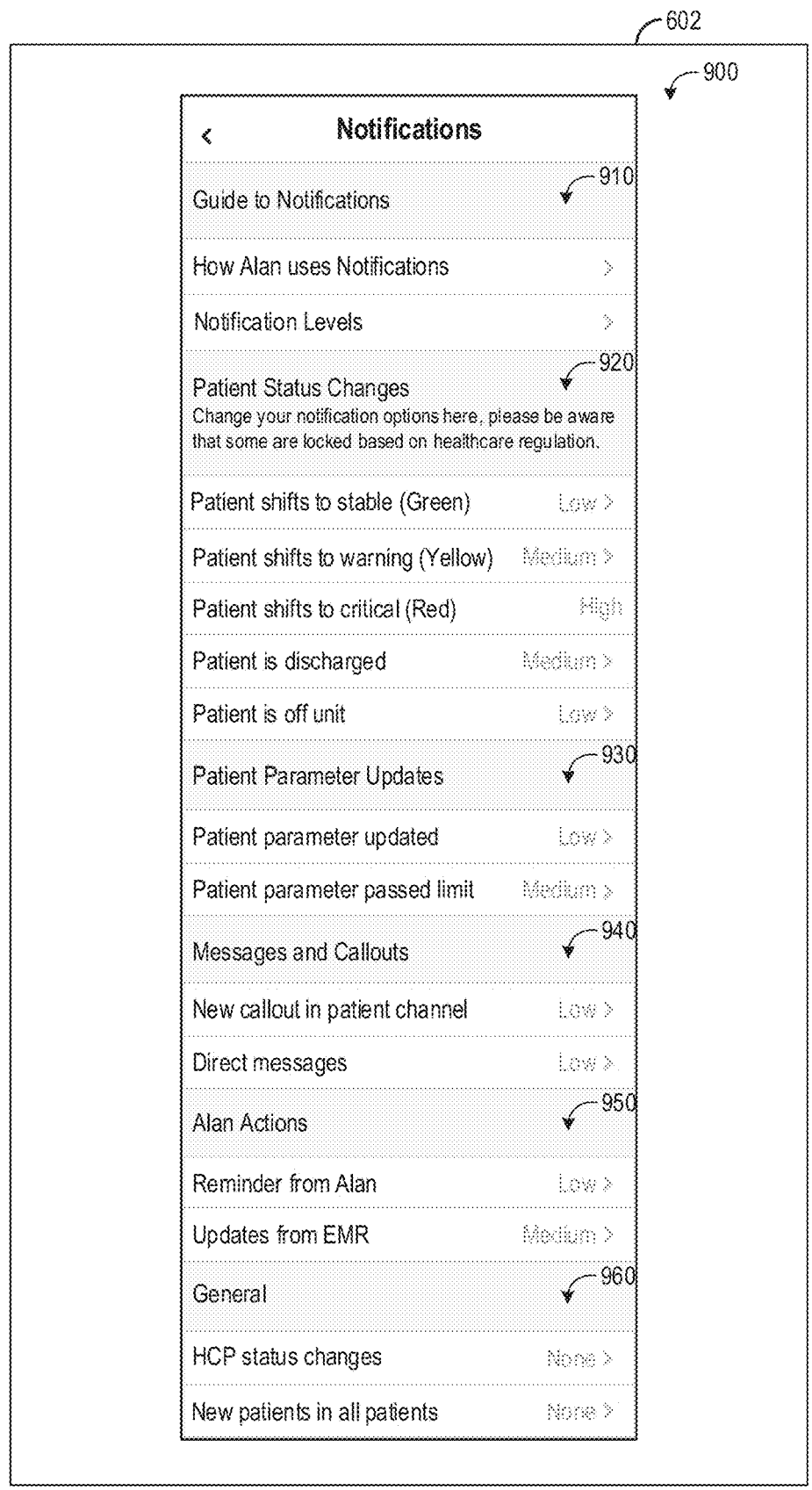
FIG. 9 shows an example display device displaying an example interface for setting notification preferences.

An example collaborative healthcare system is shown in FIG. 1. The collaborative healthcare system may be included in or associated with a medical facility and may include a communication channel comprising a communication thread and a dashboard for each admitted patient of the medical facility. The collaborative healthcare system may further include one or more virtual healthcare assistants. Communication may occur on a communication channel in the form of a communication thread (e.g., of text and/or rich media messages) between care providers of the patient and the one or more virtual healthcare assistants, as shown in FIG. 2 as well as FIGS. 7 and 10-12. Patient-specific medical information may be displayed to the care providers and/or other users via a dashboard. As shown in FIG. 3, the dashboard may be launched in response to a first selection of a link on the communication thread. The dashboard may be configured to display alerts output by the one or more virtual healthcare assistants, and the alerts may be selectable to launch a portion of the communication thread occurring on the communication channel, as shown in FIG. 4, or a full version of the communication thread. Additionally, a preview of the dashboard may be launched in response to a second selection of a link on the communication thread. Further, a collaborative system interface, as shown in FIG. 5, may be displayed on a suitable display device in order to allow a user to select a communication channel or dashboard to view. In some examples, the dashboard may take on a different visual form, as shown in FIG. 6, and a user may navigate between the dashboard and communication thread using a menu that also allows the user to access additional information pertaining to the patient. For example, via the menu, a user may access a patient timeline, as shown in FIG. 13, where relevant patient medical events and information over a predetermined time period may be displayed. Included in the timeline and/or in the communication thread, as well as displayed over any executing application on a caregiver device, may be notifications, as shown in FIGS. 8A-8C. The notifications may alert caregivers assigned to the patient of changes in patient status, relevant medical events (e.g., available lab test results), or reminders to assess patient monitoring data, such as vital signs. Users may set preferences for receipt of notifications in order to customize how the notifications are received, actions that may be performed in response to the notifications, etc., as shown in FIG. 9.

Figure 14:
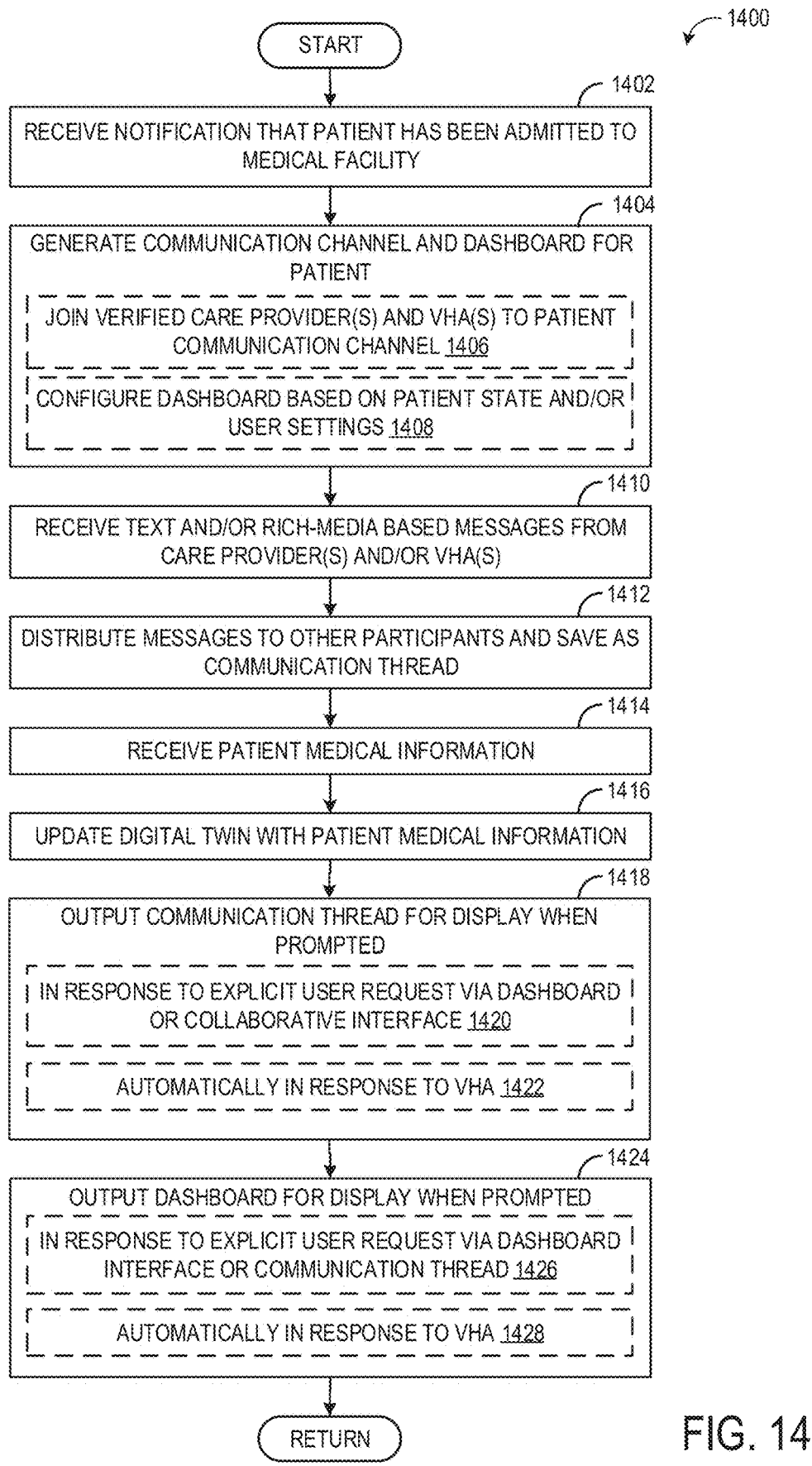
FIG. 14 is a flow chart illustrating an example method for facilitating communication within a collaborative healthcare system.

The communication thread-dashboard pairs may be generated and accessed according to the method illustrated in FIG. 14. Notifications may be generated and output according to the methods illustrated in FIGS. 15 and 16. In another example, as shown by the method of FIG. 17, a patient timeline may be assembled and output for display in response to a request from a care provider or other user.

FIG. 1 schematically shows an example collaborative healthcare system 100 that may be implemented in medical facility such as a hospital. Collaborative healthcare system 100 may include a collaborative space server system 102. Server system 102 may include resources (e.g., memory 130, processor(s) 132) that may be allocated to store and execute a communication thread, a dashboard, and a digital twin for each of a plurality of patients. For example, as shown in FIG. 1, a communication thread 104, dashboard 106, and digital twin 108 are stored on server system 102 for a first patient (patient 1); a plurality of additional communication threads, dashboards, and digital twins may be stored on server system 102, each corresponding to a respective patient (patient 2 up to patient N).

As explained above, the communication thread 104 may facilitate communication among a care provider team (which may include multiple care providers that are each providing care to the patient (e.g., patient 1)) as well as one or more virtual healthcare assistants (explained in more detail below). Messages sent on the communication thread 104 may be saved and may be accessible via the dashboard 106 (and the dashboard may be accessible via the communication thread). Further, the patient medical information, including medical history, current state, vital signs, and other information, may be entered to the digital twin 108, which may be used to gain situational awareness, clinical context, and medical history of the patient to facilitate predicted patient states, procurement of relevant treatment guidelines, patient state diagnoses, etc.

Communication occurring on communication thread 104 may be displayed on one or more suitable display devices associated with a respective care provider device and/or medical facility administration device. Likewise, dashboard 106 may be displayed on the one or more display devices. As shown in FIG. 1, a plurality of care provider devices, from a first care provider device 134, a second care provider device 136, and on up to an nth care provider device 138, may be communicatively coupled to server system 102. Each care provider device may include a processor, memory, communication module, user input device, display (e.g., screen or monitor), and/or other subsystems and may be in the form of a desktop computing device, a laptop computing device, a tablet, a smart phone, or other device. Each care provider device may be adapted to send and receive encrypted data and display medical information, including medical images in a suitable format such as digital imaging and communications in medicine (DICOM) or other standards. The care provider devices may be located locally at the medical facility (such as in a nurses station or in the room of a patient) and/or remotely from the medical facility (such as a care provider's mobile device).

When viewing communication thread 104 and/or dashboard 106 via a display of a care provider device, a care provider may enter input (e.g., via the user input device, which may include a keyboard, mouse, microphone, touch screen, stylus, or other device) that may be processed by the care provider device and sent to the server system 102. In examples where the user input is a message to be sent to other care providers and/or one or more virtual healthcare assistants, the message may be sent to the server system 102, where the message may be saved as part of the communication thread 104 and then the server system 102 may send the message to other verified participants on the communication channel (e.g., the other care providers and/or one or more virtual healthcare assistants that are joined to the communication channel). In examples where the user input is a selection of a link or user interface control button of the dashboard, the user input may trigger display of the communication thread, trigger progression to a desired state of the dashboard (e.g., trigger display of desired patient medical information), trigger updates to the configuration of the dashboard, or other actions.

The collaborative space server system 102 may be communicatively coupled to hospital operational systems 118. The hospital operational systems 118 may store and/or control a variety of hospital-, care provider-, and patient-related information, including but not limited to patient admission information (including date of admission and location of the patient within the medical facility), patient care protocols and workflows, and care provider information including which care providers are monitoring/treating which patients. Further, the hospital operational systems 118 may be communicatively coupled to a plurality of monitoring devices 120, an electronic medical records (EMR) database 122 (described in more detail below), and one or more of the care provider devices. The monitoring devices 120 may include traditional medical devices monitoring respective patients, such as pulse oximeters, heart rate monitors, blood glucose monitors, and ECGs, as well as microphones, cameras, and other devices. The monitoring devices 120 may send output directly to the server system 102 and/or may send output to the hospital operational systems 118, EMR database 122, and/or one or more care provider devices. For example, a plurality of monitoring devices monitoring patient 1 may be configured to send output to the server system 102 and the server system 102 may be configured to send some or all of the data output by the monitoring devices to a care provider device (such as care provider device 134). Further, in some examples, server system 102, hospital operational systems 118, and/or EMR database 122 may receive diagnostic imaging information obtained from one or more imaging modalities, such as ultrasound, CAT, MM, X-ray, etc.

The hospital operational systems 118 may direct creation of and control access to each communication thread and dashboard. For example, when a patient is admitted, the hospital operational systems 118 may associate the patient with an identifier (e.g., an identification code) and notify the collaborative space server system 102 to generate a communication channel for that patient. When a care provider is assigned to assist in management/treatment of the patient, the hospital operational systems 118 may notify the collaborative space server system 102 to join that care provider to the patient's communication channel (the care provider may also be associated with an identifier which may be used to identify the care provider and appropriately distribute messages sent and received on the channel). In this way, the hospital operational systems 118 may control who has access to patient information. In some examples, hospital operational systems 118 and/or server system 102 may control levels of accessibility to patient information depending on the location of a care provider device (e.g., devices located at the medical facility may have access to more patient information than devices located remotely from the medical facility). Additional information about the hospital operational systems 118 is presented below.

Collaborative space server system 102 may further store instructions for (e.g., in memory 130) and be configured to execute (e.g., via processor(s) 132) a plurality of virtual healthcare assistants (VHAs). As shown, collaborative space server system 102 includes an electronic medical record (EMR) VHA 110, a guideline VHA 112, a predictive VHA 114, a listening VHA 116, and a monitoring VHA 117. The VHAs may be realized as several VHAs each for a different purpose, as described herein, various groups of VHAs (e.g., a the guideline VHA 112 and predictive VHA 114 may be combined into one VHA that is configured to both diagnose or predict patient state and output relevant guidelines), or as one overall VHA, which represents all the different attributes that will be hereby elaborated. All activations of VHAs by human care providers may be performed by using natural language including medical language, either by text or by voice.

EMR VHA 110 is configured to retrieve patient information from an electronic medical record database, such as EMR database 122, and present the retrieved data via the communication thread and/or dashboard. For example, a care provider may send a request to the EMR VHA 110, through the communication channel, for a particular piece of patient medical history saved in an EMR of the patient. The EMR VHA 110 may receive the request and determine, from the natural language of the text, that the piece of patient medical history has been requested. The EMR VHA 110 may obtain the piece of medical history from EMR database 122. The EMR VHA 110 may then send the piece of medical history to the care provider in the form of a message on the communication thread 104. In some examples where the requested piece of medical history is also saved in the digital twin 108, EMR VHA 110 may be configured to retrieve the medical history from the digital twin 108.

EMR database 122 may be an external database accessible by EMR VHA 110 via a secured hospital interface, or EMR database 122 may be a local database (e.g., housed on a device of the hospital). EMR database 122 may be a database stored in a mass storage device configured to communicate with secure channels (e.g., HTTPS and TLS), and store data in encrypted form. Further, the EMR mass storage device is configured to control access to patient electronic medical records such that only authorized healthcare providers may edit and access the electronic medical records. An EMR for a patient may include patient demographic information, family medical history, past medical history, lifestyle information, preexisting medical conditions, current medications, allergies, surgical history, past medical screenings and procedures, past hospitalizations and visits, etc.

Thus, the EMR VHA 110 serves as a connection to the EMR database. The EMR VHA may interpret questions by the human care providers regarding the patient and allows querying of the EMR database for relevant information regarding the patient (e.g. "what was the average systolic blood pressure in the last four hours?" or "show me the trend of the O2 saturation"). Queries can implicitly relate to the patient's status or medical history. The EMR VHA 110 also allows EMR-generated alerts to be formatted and sent into the patient communication thread (in a configurable manner either by a "setting" option or by voice command, such as telling it, e.g., "don't show me this again"). The EMR VHA 110 may also serve as a drug safety alerting system (including allergies, drug-to-drug relations, etc.) and may be thus connected to a relevant medical knowledgebase.

Guideline VHA 112 is configured to retrieve relevant care guidelines from an external guideline service 124. Guideline VHA 112 may be prompted, via communication occurring on communication channel, to retrieve care guidelines. For example, a care provider may explicitly request care guidelines for a given condition, such as sepsis, on the communication thread and guideline VHA 112 may query external guideline service 124 in response to the explicit request. In other examples, guideline VHA 112 may determine implicitly that care guidelines for a given patient condition are being requested and/or may be helpful. For example, guideline VHA 112 may parse communication on the communication thread 104 (e.g., between one or more care providers and/or a suitable VHA) to determine that guidelines are being requested (e.g., rather than receiving an explicit request for the guidelines, guideline VHA 112 may determine that two care providers are discussing guidelines and may retrieve the guidelines without being requested to do so). In a further example, guideline VHA 112 may determine, from patient vital signs (e.g., output by the one or more monitoring devices 120), digital twin 108, and/or other sources that a patient may be undergoing a given condition (e.g., high heart rate) and may automatically obtain guidelines for treating the condition.

External guideline service 124 may be a remote service accessed via a network, or external guideline service 124 may be a local service executed on a computing device of the hospital. The care guidelines obtained from external guideline service 124 may be preconfigured by protocols and guidelines that are specific to the medical facility that the collaborative space server system 102 services. Further, external guideline service 124 may include differential diagnoses trees that guideline VHA 112 may access to determine potential diagnoses based on a patient condition or state.

For example, with regards to the patient's state and medical history as search terms, e.g., if a diabetic patient has a high sequential organ failure assessment (SOFA) score and high glucose levels, specific guidelines will be queried without additional query terms, or alternatively the external guideline service may be queried by specifying specific guidelines. In other words, the guideline VHA may enter specific search terms to the guideline service based on patient state and symptoms (e.g., diabetes, SOFA score of five, glucose level of 190 mg/dL) to obtain one or more potential diagnoses and/or guidelines, or the guideline VHA may specifically ask for guidelines for a given condition (e.g., sepsis). The guideline VHA may also serve as a source for generating reminders for treatments that are part of a care protocol or to keep track of what decision-driving tests have been completed and what are still needed to complete the protocol. A change in patient status may be a trigger for automatic notification of relevant guidelines. The guideline VHA may also be used to plan a trajectory for the patient, of both disease progression and a care path. A patient trajectory may be determined based on the combined trajectories of vital signs, laboratory test results, or other data for that specific patient. In defining a patient trajectory, the guideline VHA may assist care providers to adjust care pathways or to stay the course and give early warning if the patient deviates from the planned traj ectory.

Predictive VHA 114 is configured to retrieve predictions of future patient states from an external prediction service 126. Predictive VHA 114 may detect and issue alerts on relevant changes in the patient's state (e.g., small but worrying changes in vital signs, changes in qSOFA score). Predictive VHA 114 may also predict future events (e.g., a prediction of sepsis being developed in the coming four hours) by connecting to external prediction service 126. Predictive VHA 114 may query external prediction service 126 with search terms indicating current and/or past patient state (e.g., blood pressure trend, glucose level trend, etc.). If prediction service 126 outputs a possible future condition, the predictive VHA 114 may send an alert into the communication thread, as text, and may provide supplemental information regarding the alert. The predictive VHA 114 may also track the response of human care providers as reflected in the communication channel or in the EMR orders registry. The predictive VHA 114 may obtain patient data from the EMR and different online monitoring devices 120 (ECG, cameras, etc.) as represented in the digital twin.

Listening VHA 116 is configured to monitor communication on the communication thread 104 as well as actual human voice communication to obtain/infer various information related to the patient. In doing so, listening VHA 116 serves as a monitor, by listening to the events in the patient's surroundings including medical staff conversations and patient input (from moaning to speech). The monitored conversations/inputs may be used to record the patient's status (for EMR/digital twin) or to infer clinician reasoning (e.g., the listening VHA may catch an order to prescribe a certain antibiotic by a doctor, and understand an infection is suspected). The listening VHA 116 may receive output from one or more microphones positioned in proximity to the patient, for example, in order to monitor the conversations and inputs.

Monitoring VHA 117 is configured to receive output from the monitoring devices 120 and may track a patient condition or state based on the received output. In some examples, monitoring VHA 117 may present the received data via the communication thread and/or dashboard. For example, a care provider may send a request to the monitoring VHA 117, through the communication channel, for a particular piece of patient monitoring data, such as current heart rate. The monitoring VHA 117 may receive the request and determine, from the natural language of the request, that the patient medical data has been requested. The monitoring VHA 117 may obtain the patient medical data from the relevant monitoring device of the monitoring devices 120. The monitoring VHA 117 may then send the medical data to the care provider in the form of a message on the communication thread 104. In some examples, monitoring VHA 117 may be configured to save the medical data at the digital twin 108. Further, medical data received by monitoring VHA 117 may be displayed via the dashboard. In some examples, monitoring VHA 117 may obtain patient medical data only in response to a request from a care provider. In other examples, additionally or alternatively, monitoring VHA 117 may obtain medical data from the monitoring devices 120 independently of care giver request, and may output requested medical data when a care giver requests the data and/or when the received medical data is detected (by the VHA) as being abnormal, having changed, or otherwise indicative of an urgent patient state. In some examples, monitoring VHA 117 may be configured to provide received medical data to predictive VHA 114 and/or guideline VHA 112 in order to predict a future patient state based on current patient medical data and/or retrieve relevant care guidelines based on current patient medical data.

The VHAs may be configured to receive messages from human care providers and utilize natural language processing to determine what information is being conveyed in the messages. For example, the VHAs may utilize natural language processing to determine if a message received on the communication channel includes a request for patient medical information, and if so, determine what medical information is being requested. The VHAs may also be configured to process medical information of the patient (e.g., vital signs, medical history, current symptoms) received from the patient EMR, the monitoring devices, the care providers, and/or other sources and determine which parameters of the medical information may be used (e.g., entered into the guideline or prediction service) to determine a patient state (such as determine the likelihood the patient is experiencing a certain condition, such as sepsis). The VHAs may execute deep learning models (e.g., machine learning or other deep learning models such as neural networking) that are trained to understand medical terminology. Further, the deep learning models may be configured to learn updates or modifications to the models in an ongoing manner in a patient and/or care provider specific manner. For example, a predictive VHA may execute a deep learning model that is trained to determine that low blood pressure may be a symptom of relevance that should be entered into a prediction service or diagnosis tree, but then may be trained for a specific patient that low blood pressure for that patient is benign and may have less relevance.

The models may be trained in a suitable manner. In a first example, the models may be rule-based assistants that are configured with a set of answers for predetermined, likely questions. When a VHA receives a question, the VHA may be configured to output an answer from the set of answers. In a second example, the models may include directed acyclic graphs (DAG) of states, each of which include rules for how to react and how to proceed to various questions. However, such VHAs may only be configured to respond when there is a clear indication of the user intent (e.g., the user presses on a button "obtain heart rate") and entities (answer to "please provide the patient's date of birth" with a date).

Thus, the VHAs described herein may include artificial intelligence and be adapted to handle natural language which is a way to take human input and map it to intent and entities. The VHAs may be adapted to hold a state and map the state with (intent, entities) to an actionable API. The mapping may be performed by teaching machine learning models by providing the models with examples of such mappings. If a VHA is autonomous, the VHA may include a prediction or other mechanism that may trigger the VHA to initiate communication. The VHAs may also be configured to vary their reactions to make the VHAs more human like (this may also be performed by providing examples to a machine learning training algorithm).

Further, the training mechanism utilized may be specific for different VHAs. For example, the listening VHA (and the natural language processing engines of the other VHAs) may execute deep networks trained for natural language with medical language. This may be combined with taxonomies from the medical domain. The EMR VHA and the guideline VHA may receive the output (intent and entities) from the listening VHA and/or the respective natural language processing engine and map the output to queries. The VHAs may be trained by having examples of the best results of existing queries. The predictive VHA may be trained on its own clinical task. For example, if the predictive VHA is to predict if a patient will survive early release from an intensive care unit, then the predictive VHA may be trained on data of patients that were in the ICU and were released at different stages.

Additional VHAs may be included on the server system, such as VHAs specific to a patient state. Such an example may include a sepsis VHA that may only be joined to a patient communication channel when that patient is undergoing or at risk of developing sepsis. The sepsis VHA may be trained to specifically predict sepsis, obtain treatment guidelines for sepsis, suggest optimal lab tests to diagnose sepsis and/or monitor sepsis progression, and/or suggest treatment options for sepsis. Other VHAs may include a patient comfort VHA (e.g., a VHA configured to detect or predict patient pain, discomfort, hunger, or other symptoms not necessarily indicative of a particular medical condition but which care providers may want to be notified of to improve patient comfort), a communication VHA (e.g., that parses communication from care givers and facilitates sharing of information among the VHAs), and/or other VHAs. Further, various configurations of VHAs not disclosed above are within the scope of this disclosure, such as related VHAs being grouped into a single VHA (e.g., the monitoring and EMR VHAs being combined as one medical data VHR). For example, a single VHA may be trained for all of the above-described VHA possible skills.

A global view of multiple or all patient communication thread-dashboard pairs may be provided via to one or more of the care provider devices and the hospital operational systems 118. For example, the choice of the specific thread/dashboard pair to access may be controlled by an access application executing on collaborative space server system 102 that allows to a user to view all the relevant patients (for example, communication thread-dashboard pairs for all the patients being treated/monitored in a nurses station may be accessed on a workstation at the nurses station, or communication thread-dashboard pairs for all the patients being treated/monitored by a given care provider may accessed by that care provider on his or her mobile device). In some examples, alerts and important events within all the relevant communication channels will be signified in the global view. The choice to go into a specific communication channel may be made by a user picking the patient in the global view (or by an explicit voice command), but may be also be automated using automatic mechanisms which may detect the position of the care provider in respect to a patient (such as via BLUETOOTH® when entering a patient's proximity or based the context of a detected discussion).

The access application may allow export of only specific widgets (such as the blood pressure graph of a patient) of a communication thread and/or dashboard, or may allow more compound parts (such as a patient dashboard or a portion of the thread) to selected external applications and/or devices. For example, as explained above, devices located off-site of the medical facility may only be allowed access to some of the patient medical data, and the access application may control which patient medical data is viewable outside of the medical facility.

A management application executed on hospital operational systems 118 and/or collaborative space server system 102 may allow an administrator to update the care team that has access to a patient's communications channel, as described above. The management application may include an interface for configuring hospital specific protocols and care guidelines. The management application may also aggregate information from the communication channels to be used to predict needs for hospital operations, presenting forecasts for capital, disposable, and human assets based on aggregate acuity or disease statistics. Moreover, analytics of the information on the communication channel may be employed to improve the system and its predictors.

Collaborative space server system 102 includes a communication module 128, memory 130, and processor(s) 132 to store and execute the communication channel-dashboard pairs, digital twins, and VHAs, as well as send and receive communications, graphical user interfaces, medical data, and other information.

Communication module 128 facilitates transmission of electronic data within and/or among one or more systems. Communication via communication module 128 can be implemented using one or more protocols. In some examples, communication via communication module 128 occurs according to one or more standards (e.g., Digital Imaging and Communications in Medicine (DICOM), Health Level Seven (HL7), ANSI X12N, etc.). Communication module 128 can be a wired interface (e.g., a data bus, a Universal Serial Bus (USB) connection, etc.) and/or a wireless interface (e.g., radio frequency, infrared, near field communication (NFC), etc.). For example, communication module 128 may communicate via wired local area network (LAN), wireless LAN, wide area network (WAN), etc. using any past, present, or future communication protocol (e.g., BLUETOOTH™, USB 2.0, USB 3.0, etc.).

Memory 130 one or more data storage structures, such as optical memory devices, magnetic memory devices, or solid-state memory devices, for storing programs and routines executed by processor(s) 132 to carry out various functionalities disclosed herein. Memory 130 may include any desired type of volatile and/or non-volatile memory such as, for example, static random access memory (SRAM), dynamic random access memory (DRAM), flash memory, read-only memory (ROM), etc. Processor(s) 132 may be any suitable processor, processing unit, or microprocessor, for example. Processor(s) 132 may be a multiprocessor system, and, thus, may include one or more additional processors that are identical or similar to each other and that are communicatively coupled via an interconnection bus.

As used herein, the terms "sensor," "system," "unit," or "module" may include a hardware and/or software system that operates to perform one or more functions. For example, a sensor, module, unit, or system may include a computer processor, controller, or other logic-based device that performs operations based on instructions stored on a tangible and non-transitory computer readable storage medium, such as a computer memory. Alternatively, a sensor, module, unit, or system may include a hard-wired device that performs operations based on hard-wired logic of the device. Various modules or units shown in the attached figures may represent the hardware that operates based on software or hard-wired instructions, the software that directs hardware to perform the operations, or a combination thereof.

"Systems," "units," "sensors," or "modules" may include or represent hardware and associated instructions (e.g., software stored on a tangible and non-transitory computer readable storage medium, such as a computer hard drive, ROM, RAM, or the like) that perform one or more operations described herein. The hardware may include electronic circuits that include and/or are connected to one or more logic-based devices, such as microprocessors, processors, controllers, or the like. These devices may be off-the-shelf devices that are appropriately programmed or instructed to perform operations described herein from the instructions described above. Additionally or alternatively, one or more of these devices may be hard-wired with logic circuits to perform these operations.

One or more of the devices described herein may be implemented over a cloud or other computer network. For example, server system 102 is shown in FIG. 1 as constituting a single entity, but it is to be understood that server system 102 may be distributed across multiple devices, such as across multiple servers.

While not specifically shown in FIG. 1, additional devices described herein (care provider device 134, care provider device 136, and care provider device 138, hospital operational systems 118, monitoring devices 120, EMR database 122, external guideline service 124, external prediction service 126) may likewise include user input devices, memory, processors, and communication modules/interfaces similar to communication module 128, memory 130, and processor(s) 132 described above, and thus the description of communication module 128, memory 130, and processor(s) 132 likewise applies to the other devices described herein. As an example, the care provider devices (e.g., care provider device 134) may store user interface templates in memory that include placeholders for relevant information stored on server system 102. For example, care provider device 134 may store a user interface template for a patient dashboard that a user of care provider device 134 may configure with placeholders for desired patient information. When the dashboard is displayed on the care provider device, the relevant patient information may be retrieved from server system 102 and inserted in the placeholders. The patient information may include current patient vital signs, VHA alerts, desired patient state trends, or other information, as explained in more detail below. The user input devices may include keyboards, mice, touch screens, microphones, or other suitable devices.

FIG. 2 shows an example communication thread 200 of a patient-specific communication channel, and as such may be a non-limiting example of communication thread 104. Communication thread 200 may be displayed on a display device 202. Display device 202 may include a screen on which the communication thread is displayed and may be coupled to and/or included as a part of a computing device, such as care provider device 134. Communication thread 200 may be displayed in response to a user request to display the communication thread. For example, the user (e.g., a care provider) may access a collaborative system interface that includes a global view of all communication threads and dashboards the user is authenticated to participate in (which may include all patients at the medical facility the care provider is attending to) and may select a desired communication thread to view. An example collaborative system interface 500 is shown in FIG. 5. Collaborative system interface 500 may be displayed on display device 202 or other suitable device and may include all patients admitted to a specific unit or ward of a medical facility. As shown, collaborative system interface 500 includes identifying information specifying the medical facility ("acute care center") and relevant unit ("ward 1") of the medical facility, and further includes links to patient-specific communication threads and dashboards for the patients in that unit of that medical facility. However, in other examples, the patients shown via collaborative system interface 500 may specific to a certain care provider.

Collaborative system interface 500 may include a notification section whereby the user viewing collaborative system interface 500 may be notified of urgent patient conditions, active communication channel discussions, lab test results, and other information. For example, collaborative system interface 500 includes a notification section that shows that one patient requires attention (e.g., due to deteriorating vital signs) while two new discussions are available. While collaborative system interface 500 provides a mechanism via which a care provider may be notified of important/relevant information (such as a patient's deteriorating vital signs), the collaborative system interface 500 may not be configured to notify a care provider of the important/relevant information in a time-sensitive manner, particularly when the care provider is not interacting with the collaborative system interface 500. Thus, as will be described in more detail below, collaborative space server system 102 may be configured to, via one or more VHAs, output notifications that may be displayed on a care provider's device regardless of what applications are or are not executing on the care provider's device, so that the care provider may be notified of important and time-sensitive information, in a manner that is customizable by the care provider.

Collaborative system interface 500 further includes links to patient communication thread-dashboard pairs. For example, FIG. 5 shows links to communication thread-dashboard pairs for patient ID 0123, patient ID 1111, patient ID 1234, and patient ID 1235. As explained above, each patient may be assigned an identifier that may be used to identify the patient on the communication thread and dashboard. In other examples, other mechanisms for identifying the patient may be used, such as location (e.g., bed 2 in room 4) and/or actual patient name. Additional patient links may be viewed by scrolling the interface. Each patient link may include notifications where relevant. For example, the link for patient ID 1111 includes a notification that three new messages are available to be viewed on the communication channel for that patient. The link for patient ID 1234 includes a notification that action is needed (e.g., due to high blood pressure or other significant vital sign being detected, which will be explained in more detail below) as well as a notification that one new message is available on the communication channel for that patient. In some examples, when a lab test result for a patient is available, the link for that patient may include a notification of an available lab test result, such as the notification displayed in the link for patient ID 1235. In examples, care providers may be notified of available lab test results through the communication channel for the patient, and thus the notification may include a notification that a new message is available.

Selection of a patient link may launch the communication thread or dashboard for that patient. For example, selection of the link for patient ID 1234 may launch the communication thread 200 for patient ID 1234, shown FIG. 2 and explained in more detail below.

Returning to FIG. 2, communication thread 200 may include an identification header 204 that identifies the patient being discussed/monitored via the communication thread. In the illustrated example, communication thread 200 is specific to patient ID 1234. In the illustrated portion of communication thread 200, communication is occurring between a care provider (e.g., Dr. Smith) and a virtual healthcare assistant that, in the illustrated example, has a human persona and as such includes a human name (Alan). Communication thread 200 is being viewed by Dr. Smith, although any authenticated/approved user may view communication thread 200. As shown by the first message from the top, Dr. Smith is requesting medical information relating to the patient from the VHA by asking, in natural language, for a heart rate graph ("Could I get the HR graph please"). In response, the VHA sends an image of the patient's heart rate graph, which may be obtained or assembled from the patient's EMR data. The image of the heart rate graph is viewable in the communication thread and may also be selected via suitable user input to view in a different form, such as via the patient dashboard.

At a later time (e.g., 4:00 PM), the VHA outputs an alert/notification in the communication thread indicating a change in patient status, herein a deterioration in vitals. The alert is accompanied by a suggested course of action that a care provider may take, including checking respiratory rate and mental state. The VHA issues another alert at 5:00 PM indicating that sepsis is suspected based on a quick SOFA score (qSOFA), owing to low systolic blood pressure and a low Glasgow coma scale. The alerts issued by the VHA may include links to the patient dashboard, for example, allowing a user to select a link to launch the dashboard and view the medical data relating to the alerts. For example, the alert "systolic BP is less than 100 mmHg" is shown in underline, indicating a link to additional information is available. A user may select the link via a suitable input, such as via a mouse click, touch input, or voice command. In some examples, selecting a link with a first selection (e.g., a double click) may launch the patient dashboard (as shown in FIG. 3). Selecting a link with a second selection (e.g., a single click or a hover) may launch a preview where only the patient's blood pressure graph is shown.

In response to the alert regarding the potential sepsis, Dr. Smith asks for guidelines at 5:01 PM. Because the VHA had immediately previously issued the alert regarding the possible sepsis due to the qSOFA score, the VHA may assume that the guidelines being requested by Dr. Smith include guidelines for sepsis based on a qSOFA score. In response, the VHA retrieves guidelines from an external guideline service relating to qSOFA scores and outputs the guidelines into the communication thread. As shown, only a portion of the guidelines are displayed in the communication thread. By selecting the link (the underlined "qSofa guidelines"), the user may be taken to a different interface where the full guidelines are displayed, or the full guidelines may be displayed over the top of the still-displayed communication thread.

While not shown in FIG. 2, communication thread 200 may include a search box/functionality where a user may search for past messages on the communication thread. For example, a user may enter a command (by voice or text) requesting that all messages related to the patient's heart rate be displayed. Also displayed on display device 202 is a communication thread button 206 and a dashboard button 208. In FIG. 2, the user is viewing the communication thread 200 occurring on the communication channel. Hence, the communication thread button 206 is highlighted. To switch to the dashboard for patient ID 1234, the user may select the dashboard button 208. Additionally or alternatively, the user may request to view a vital signs interface by selecting a link within the identification header 204 (e.g., by selecting "vitals"). The vital signs interface, which is discussed in more detail below with respect to FIG. 6, may serve as an additional or alternative dashboard, wherein additional medical information of the patient may be displayed. The user may request to view additional interfaces via the identification header 204, such as a labs interface, where lab results may be displayed, a meds interface, where medicine dosage, timing, and other information may be displayed, and an orders interface, where testing orders (such as diagnostic imaging tests, lab tests, or other tests) may be displayed.

As explained above, FIG. 2 shows communication between a care provider and a virtual healthcare assistant ("Alan"), where Alan provides all the information requested by the care provider as well as provides alerts/notifications. In this way, Alan is performing the functions described above with respect to FIG. 1 ascribed to the predictive VHA, EMR VHA, and guidelines VHA. It is to be understood that in some examples, each of the different VHAs may interact with the communication thread individually.

FIG. 3 shows an example dashboard 300 that may be displayed on display device 202 or other suitable device. Dashboard 300 may be displayed in response to a user input to the communication thread 200, for example by selecting a link within medical information displayed in communication thread, as explained above, or in response to selection of the dashboard button 208. However, dashboard 300 may be displayed in response to other inputs, such as in response to a user input selecting the dashboard from the collaborative system interface of FIG. 5 that includes a global view of multiple communication threads and dashboards. Additionally, FIG. 3 shows a side bar 302 displayed along with dashboard 300 showing patient dashboards for the patients Dr. Smith is currently attending. User input to the side bar may launch a different dashboard, for example Dr. Smith may select to view each of the currently available dashboards to quickly assess the status of each patient.

Dashboard 300 may be configured to display patient medical information based on the current patient state and user-configured settings. For example, a dashboard for a patient that is being treated at the medical facility for pneumonia may be configured to display different medical information than a dashboard for a patient that is being treated at the medical facility for a stroke. In some examples, when a patient is admitted at the medical facility, a dashboard may be generated automatically for the patient based on the reason of admittance (e.g., pneumonia), thereby including the most relevant patient medical information for the patient's condition, such as blood oxygen level and respiration rate. A user may also configure which medical data to view via the dashboard, for example a doctor attending to the patient may choose to view heart rate rather than respiration rate.

The medical information that is displayed on the dashboard may be obtained from one or more monitoring devices currently monitoring the patient, such that the medical information is displayed on the dashboard in a real-time (or near real-time) manner. Additionally or alternatively, the medical information that is displayed on the dashboard may be obtained from the patient's EMR, the digital twin associated with the patient, and/or the communication thread. As explained above, one or more VHAs may obtain patient medical information from the patient's EMR, the monitoring devices, guideline services, or other sources and include the obtained medical information as a message in a communication thread on the communication channel. To view the medical information in greater detail, the user may select the medical information from the communication thread, where the medical information may then be displayed in the dashboard.

Additional information may also be displayed via the dashboard, such as patient information (location, demographics, medical history), care provider information (such as which doctors, nurses, and/or other care providers are attending to the patient), and a timeline of selected or relevant messages from the communication thread. For example, the most recent alerts may be displayed as a timeline on the dashboard.

Referring to dashboard 300 as an example, patient information 304 is displayed at the top of the dashboard, including patient identification and location. Care provider information 306 is also displayed in dashboard 300, including current care providers for the patient. Additionally, a user interface control button 308 is shown that, when selected, may allow the care provider viewing dashboard 300 to view and interact with the communication thread.

Dashboard 300 further includes real-time medical information indicators 310. As shown, the indicators 310 include a SOFA score and blood glucose level, depicted as gauge charts with respective needles that move to indicate current SOFA score and blood glucose relative to a range of possible SOFA scores and blood glucose levels. While not shown in FIG. 3, the gauge charts may include color coding for quick determination of normal, intermediate, and high scores/levels, for example. The gauge charts shown are exemplary in nature and patient medical information may be shown in other forms.

Dashboard further includes medical history trends, including a first graph 312 depicting mean arterial blood pressure trend (e.g., blood pressure as a function of time) and a second graph 314 depicting blood glucose trend (e.g., blood pressure as a function of time). The medical history trends shown in FIG. 3 may be displayed on the dashboard in response to a request from a user (e.g., in response to a care provider selecting a link to patient medical history from a communication thread), due to a preconfigured dashboard setting, or other suitable trigger. For example, as shown in FIG. 2, the VHA issued an alert at 5:00 PM that included reference to patient blood pressure in the form of a link. When the link is selected (e.g., via cursor 204), the dashboard 300 may be displayed showing the first graph 312 of the patient's blood pressure trend.

Dashboard 300 further includes a recent lab test results section 316, where the results from recent lab tests may be displayed. For example, the user may have selected a link to available procalcitonin (PCT) test results displayed as part of a communication thread, which may result in display of dashboard 300. Via the recent lab test results section 316, the user (care provider) may be notified that the PCT test for that patient is relatively high and thus sepsis is confirmed or suspected.

As explained earlier, one or more of the virtual healthcare assistants may be configured to monitor patient vital signs, via the output from the monitoring devices, the information stored in the digital twin, or other source. If a vital sign (or other health parameter) meets a predetermined condition, the one or more virtual healthcare assistants may be configured to output an alert to notify the one or more care providers attending the patient that patient follow-up may be needed. The alerts may be included in the communication thread, as discussed above. Additionally or alternatively, the alerts may be displayed on the dashboard. As shown, first graph 312 includes two alerts, each alert issued when mean arterial blood pressure dropped below a threshold, such as 80 mmHg, or trended in an unexpected way, such as five consecutively decreasing values which may or may not be below the 80 mmHg threshold. Selection of an alert may trigger display of a portion of the communication thread occurring on the communication channel where the alert was referenced.

Thus, as shown in FIG. 4, in response to user input selecting the second alert displayed on the dashboard 300 (e.g., the "alert 2" box) via cursor 204, a portion 402 of the communication thread 200 shown in FIG. 2 is displayed over dashboard 300. The portion 402 displayed may include only the portion of the communication thread that references the medical information that triggered the alert, and may also include additional messages around the message referencing the alert, in order to place the alert in context. In this way, a user may be able to quickly determine what else may have occurred around the time the alert was issued, determine if attending care providers administered treatment, or determine other relevant information. The portion 402 may not include the most recent messages in the communication thread, in some examples. Further, a user may not have access to the full communication thread when viewing the portion, and may not be able to interact (e.g., send messages) with the communication channel. Thus, a different selection on the dashboard may enable a user to view the full communication thread.

Additionally or alternatively, when viewing the portion of the communication thread, the user may scroll to view other portions of the communication thread or may enter another input to the portion of the communication thread to enable viewing of the full version of the communication thread. Alternatively, instead of showing a snippet from the communication channel, the full version of the communication thread may be displayed, with the focus point being the point in the communication channel that references the alert (which may enable the user to look before and after that point of the thread if desired). In another example, only the snippet of the communication thread may be displayed and if the snippet is selected, the full version of the communication thread may be displayed. In this way, either automatically or upon a further user input, the user may be able to interact with the communication thread (e.g., send a message via the communication thread).

Thus, the collaborative healthcare system shown in FIG. 1 may generate communication channel-dashboard pairs for each patient associated with the collaborative healthcare system. The collaborative healthcare system may include one or more computing devices, such as the care provider device 134. The computing device may include a display screen, and the computing device may be configured to display on the screen a dashboard. The dashboard may include patient medical information, such as diagnostic lab test information (e.g., lab test results, pending lab tests that have been ordered but not yet fulfilled, status updates for pending lab tests, and so forth). The computing device may additionally be configured to display on the screen an alert related to the patient medical information. For example, as shown in FIG. 3, dashboard 300 may be displayed on a screen of a computing device (e.g., display device 202, which may be a screen of a computing device such as care provider device 134). Dashboard 300 may display patient medical information, such as the graph of the blood pressure trend of the patient (e.g., first graph 312) and recent lab results. The displayed medical information may include an alert, such as alert 2 shown on first graph 312.

The alert may be selectable to launch a communication thread between a care provider and a virtual healthcare assistant. For example, as shown in FIG. 4, selection of alert 2 launches a communication thread between a care provider (Dr. Smith) and a virtual healthcare assistant (Alan). The selection of the alert enables a portion of the communication thread that references the displayed patient medical information to be seen within the communication thread. For example, FIG. 4 shows that in response to selection of alert 2, a portion 402 of the communication thread 202 (shown in FIG. 2) is displayed. The portion 402 includes reference to patient blood pressure, which is also displayed on the patient dashboard. Further, the alert may be displayed on the dashboard (at least initially) while the communication thread is in an un-launched state. For example, the alert may be displayed on dashboard 300 without display of the communication thread, e.g., while the communication thread is un-launched. In some examples, the full communication thread may be displayed rather than just a portion, with the full communication thread focused at the portion that references the patient blood pressure. According to some embodiments, the communication thread and the dashboard may both be displayed simultaneously on the display device.

In this way, the computing device provides a specific manner of displaying a limited set of information (e.g., the portion of the communication thread that specifically references medical information displayed on the dashboard) to the user, rather than using conventional user interface methods to display a generic index/list on a computer that may require the user to step through multiple menus and/or lists of communications and alerts to find the relevant portion of communication regarding the medical information. The dashboard interface-communication thread link disclosed herein may be advantageous because it avoids a user having to scroll around and switch views multiple times to find desired data/functionality, thereby preventing drilling down through many layers to get the desired data/functionality which may be slow, complex, and difficult to learn. The disclosed dashboard interface-communication thread link may improve the efficiency of using the computing device by bringing together the portion of the communication thread most relevant to the user (as it relates to the displayed medical information) and the dashboard actually displaying the medical information, allowing the user to view the most relevant information on the communication thread without actually opening up the communication thread. The speed of a user's navigation through various views and windows may be improved because the disclosed link between the dashboard and the communication thread saves the user from navigating to the communication thread from the dashboard, opening the communication thread up, and then navigating within the communication thread to enable the portion of interest to be seen or a function of interest to be activated.

Thus, the collaborative healthcare system shown in FIG. 1 may generate communication thread-dashboard pairs for each patient associated with the collaborative healthcare system. The collaborative healthcare system may include one or more computing devices, such as the care provider device 134. The computing device may include a display screen, and the computing device may be configured to display on the screen a communication thread. The computing device may additionally be configured to display on the screen a dashboard that can be reached directly from the communication thread. For example, as shown in FIG. 2, the communication thread may include a link that when selected launches a dashboard, such as the dashboard 300 shown in FIG. 3.

The communication thread displays communication between a care provider and a virtual healthcare assistant, and the communication thread includes medical information of a patient. At least a portion of the displayed medical information is selectable to launch the dashboard and enable the selected medical information to be seen within the dashboard. For example, referring to FIG. 2, the communication thread includes a link referencing patient medical information (herein, lab test results), and selection of the link launches some or all of the dashboard. The dashboard includes display of the patient medical information included in the link (e.g., the lab test results). In an example, selection of the link may launch a full version of the dashboard, as shown in FIG. 3. In another example, selection of the link may launch only a portion of the dashboard. The communication thread may be displayed while the dashboard is in an un-launched state, at least initially. For example, FIG. 2 shows the communication thread being displayed without display of the dashboard, and thus the dashboard may be unlaunched until the link the communication thread is selected.

In this way, the computing device provides a specific manner of displaying a limited set of information (e.g., the dashboard that specifically includes medical information referenced in the communication thread) to the user, rather than using conventional user interface methods to display a generic index/list on a computer that may require the user to step through multiple menus and/or lists of communications and alerts to find the relevant medical information. The communication thread-dashboard interface link disclosed herein may be advantageous because it avoids a user having to scroll around and switch views multiple times to find desired data/functionality, thereby preventing drilling down through many layers to get the desired data/functionality which may be slow, complex, and difficult to learn. The disclosed communication thread-dashboard interface link may improve the efficiency of using the computing device by bringing together the medical information most relevant to the user (via the dashboard) and the communication thread referencing the medical information, allowing the user to view the most relevant medical information discussed on the communication thread without actually accessing an electronic medical record or separate interface where patient monitoring data may be displayed. The speed of a user's navigation through various views and windows may be improved because the disclosed link between the communication thread and dashboard saves the user from navigating to an electronic medical record database, opening the database up, and then navigating within the database to enable the medical information of interest to be seen or a function of interest to be activated.

As mentioned previously, an identification header may be displayed with the communication thread and may include patient identification information and user interface control buttons via which a user may enter input selecting to view a different interface related to that patient. As an example, the identification header may include a vitals button, and user selection of the vitals button (e.g., via a touch input) may cause a vital signs interface for that patient to be displayed. FIG. 6 shows an example of a vital signs interface 600 that may be displayed on a display device 602. Display device 602 may include a screen on which the vital signs interface is displayed and may be coupled to and/or included as a part of a computing device, such as care provider device 134 shown in FIG. 1.

Vital signs interface 600 includes an identification header 604, similar to the identification header described above with respect to FIG. 2. Vital signs interface 600 further includes a plurality of patient medical parameters. The plurality of patient medical parameters may include a plurality of vital signs measured by one or more patient monitoring devices, which may be stored in the patient's EMR and/or as part of the patient's digital twin. The plurality of vital signs may include temperature, heart rate, blood pressure, mean arterial pressure, respiratory rate, O2 saturation, and oxygen level, as shown, and/or may include additional or alternative vital signs. The plurality of patient medical parameters may further include assessed patient states, which may be ascertained by one or more care providers and entered into the patient's EMR. The assessed patient states may include pain (as shown), alertness level, cognition, appearance, etc.

For each medical parameter displayed on the vital signs interface 600, a name of the medical parameter may be displayed along with the most recently-recorded value for that parameter and the time/date at which the value was recorded. For example, the first vital sign displayed from the top of the vital signs interface includes temperature with a value of 36.9° C. recorded at 14:20. For some, or all, of the patient medical parameters displayed on the vital signs interface, user selection of that medical parameter may result in additional information being displayed, such as a trend graph for that parameter that may include some or all of the measured values for that parameter over a given duration. For example, as shown, a user has selected the blood pressure parameter, e.g., by entering a touch input to the blood pressure parameter displayed on the interface. As a result, a blood pressure trend graph 606 is displayed (e.g., the blood pressure section may expand downward to accommodate the graph, shifting all other parameters below it downward). The blood pressure trend graph 606 includes six blood pressure values measured in the past 24 hours and plotted as a function of time (as each blood pressure measurement includes systolic and diastolic pressure, two curves are shown, one for systolic and one for diastolic). User deselection of the blood pressure parameter (e.g., by selecting it again) may cause the blood pressure region to collapse back to its original size and displayed information, resulting in the blood pressure trend graph not being displayed. Similar trend graphs may displayed upon user selection of any of the displayed medical parameters.

The medical parameters that are displayed as part of the vital signs interface may be selected in a suitable manner. In one example, the user may customize which parameters are displayed on the vital signs interface, whether globally for all patients that the user interacts with or individually by patient. In other examples, an administrator (e.g., of the hospital) may determine which parameters are displayed. In still further examples, additionally or alternatively, the medical parameters included in a particular patient's vital signs interface may be based at least in part on the patient's diagnosed condition(s) and/or reason for admittance to the medical unit. For example, a vital signs interface specific to a patient that is diagnosed with pneumonia may have at least some different medical parameters than a vital signs interface specific to a patient undergoing a C-section.

The vital signs interface illustrated in FIG. 6 may be displayable in addition to the patient dashboard illustrated in FIGS. 3 and 4. In this way, both the dashboard of FIGS. 3 and 4 and the vital signs interface of FIG. 6 may be available to care givers as different interfaces for viewing select patient medical information. In other examples, the vital signs interface and the dashboard illustrated in FIGS. 3 and 4 may be alternative embodiments, e.g., the vital signs interface may be one example of how a dashboard may be configured and the dashboard of FIGS. 3 and 4 may be a different example of how a dashboard may be configured. In still other examples, the vital signs interface may be a "mobile interface" and the dashboard (such as the dashboard of FIGS. 3 and 4) may be a "standard interface," such that the dashboard may be viewed when the care provider device is a desktop computer, laptop, large format monitor, etc., while the vitals interface may be displayed when the care provider device is a mobile device, such as a smartphone or tablet, or otherwise includes limited display area.

As mentioned previously, identification header 604 may include identifying information for the patient to which the displayed interface is directed to. Identification header 604 may further include a plurality of tabs/links that a user may select to launch different pages of information specific to the patient, including a chat tab, vitals tab, labs tab, meds tab, orders tab, summary tab, and timeline tab. For example, by selecting the chat tab, a communication thread specific to the patient (e.g., patient 1234) may be launched, as shown in FIG. 7. FIG. 7 illustrates an example communication thread 700 that is displayed on display device 602. Communication on communication thread 700 is occurring between a virtual healthcare assistant, herein referred to as Alan, and a care provider (Dr. Smith), as explained above with respect to FIG. 2. Communication thread 700 includes messages sent by Alan in response to Dr. Smith being joined to the communication thread for patient 1234 for the first time, and as such includes two introductory messages, first message 702 and second message 704, saying hello and informing Dr. Smith of the services Alan may be able to perform, as well as a third message 706 that includes a status update of patient 1234 (e.g., last checked vital signs).

Identification header 604, while similar to the identification header described above with respect to FIG. 2, includes additional links (e.g., tabs) not shown in FIG. 2, specifically a summary tab and a timeline tab. The summary tab, when selected, may cause a summary page for the patient to be launched. The summary page may include a distillation of the patient's medical history, reason for admittance, diagnosed conditions, and relevant patient states (e.g., vital signs, administered medications, and so forth). In this way, a care provider may access the summary page in order to quickly get up-to-date on the patient's history and current condition(s). The timeline tab, when selected, may cause a timeline page for the patient to be launched. The timeline page may include a list of relevant medical events and/or patient states over a predefined time period (such as the prior 12 hours). The relevant medical events and/or patient states may include select messages from the communication thread (as selected by one or more care providers) notifications/alerts, lab test results, and/or other information. Additional information about the timeline page will be described in more detail below.

As mentioned previously, the virtual healthcare assistant(s) may be configured to monitor patient vital signs, reception of lab test results (including diagnostic imaging results), and communication occurring on the communication thread for each of a plurality of patients, and then generate and output suitable notifications to one or more care providers when relevant/select events occur, as determined by the monitoring. As explained above with respect to FIGS. 2-4, one or more VHAs may monitor patient vital signs and output an alert when one or more vital signs meet a condition relative to a threshold (such as heart rate increasing to a threshold heart rate, blood pressure increasing to a threshold pressure or decreasing to a different threshold pressure, etc.). These alerts may be inserted into the communication thread for the specific patient, as shown in FIG. 2, as well as shown on a dashboard for the specific patient, as shown in FIG. 3. Further, as shown in FIGS. 8A-8C and explained in more detail below, the alerts (which will be referred to as notifications herein) may be output as pop-ups that may be displayed on a display device of a care provider computing device, regardless of whether the care provider is currently interacting with the computing device or regardless of what application(s) are currently launched on the computing device. In this way, the care provider may be notified of important and/or time-sensitive information relating to the patient.

To reduce "alarm fatigue" which may occur when too many notifications are pushed to a care provider, and to further assist the care provider in determining which notifications require action and which notifications may be dismissed, the notifications may be classified into a plurality of levels of importance. For example, each notification may be classified as either low importance, medium importance, or high importance based on the information being conveyed in the notification. For example, a reminder to perform a task, such as measure a patient's vital signs, may be classified as low importance. Notifications relating to patient state may be classified based on a condition of the patient, where the condition of the patient is stable, warning, or critical, as determined based on patient vital signs, for example. A notification of a small change in a patient vital sign, where the vital sign is still below a critical threshold, may be classified as medium importance. A notification of a large change in a patient vital sign and/or where the vital sign has crossed the critical threshold, may be classified as high importance. The notifications may be displayed in different colors or with different wording to indicate, at a quick glance, the level of importance of the notification. Further, as explained in more detail below, a care provider may set notification preferences that may specify what types of notifications the care provider may receive, how the notifications are displayed, what actions may occur upon reception of a notification, etc. In this way, by tailoring notifications based on care provider preferences and classifying the notifications by importance level, the risk that care providers may ignore important notifications or become unduly distracted by less important notifications may be reduced.

FIGS. 8A-8C show example notifications that may be displayed on a display device associated with a care provider device, such as display device 602. FIG. 8A shows a first example notification 800 displayed as a pop-up on display device 602. As used herein, the term pop-up refers to a graphical control element that may be displayed without explicit user input (e.g., automatically) independent of what application(s) are executing on and being displayed on the display device. Notification 800 is a low-importance notification, as notification 800 includes a reminder to take the vital signs for patient 1234. Accordingly, notification 800 may include a portion (e.g., a top half of the notification) that is displayed in a first color that signifies the low importance, such as green.

FIG. 8B shows a second example notification 810 displayed on display device 602. Similar to notification 800, notification 810 is a pop-up that may be displayed on display device 602 regardless of whether other non-related applications are currently executing (or even regardless of whether display device is in a sleep mode). For example, if an application is executing, causing other related or non-related elements to be displayed on display device, notification 810 may be displayed over the top of the other displayed elements, at least temporarily (e.g., for a predetermined amount of time, such as ten seconds, or until the notification is dismissed). Notification 810 is a medium-importance notification, as notification 810 includes an alert indicating that the status of patient 1234 has changed to a warning status (due to a change in heart rate, which is currently 110 for patient 1234). Accordingly, notification 810 may include a portion (e.g., a top half of the notification) that is displayed in a second color that signifies the medium importance, such as yellow. Further, notification 810 includes text stating that the patient status has changed from green (stable) to yellow (warning).

FIG. 8C shows a third example notification 820 displayed on display device 602. Notification 820 may be a pop-up, similar to notifications 800 and 810 described above. Notification 820 is a high-importance notification, as notification 820 includes an alert indicating that the status of patient 1234 has changed (due to a change in blood pressure), and specifically a change in status that may be indicative of a deteriorating patient condition (e.g., a blood pressure of 80/40, which may indicate a critical state of the patient). Accordingly, notification 820 may include a portion (e.g., a top half of the notification) that is displayed in a third color that signifies the high importance, such as red. Further, notification 820 includes text stating that the patient status has changed from yellow (warning) to red (critical).

FIG. 8C further includes an action menu 830 that may be displayed along with notification 820. In some embodiments, action menu 830 may be displayed with an associated notification automatically. For example, when notification 820 is displayed, action menu 830 may be displayed at the same time. In some embodiments, action menu 830 may only be displayed in response to a user request to view the action menu, such as in response to a user selection of notification 820. For example, upon notification 820 being displayed, a user may enter a touch input to notification 820, which may cause action menu 830 to be displayed.

Action menu 830 may include a plurality of control buttons, each associated with a different action related to notification 820. For example, as shown, action menu 830 includes a "go to patient" button, a "snooze" button, and a "dismiss" button. A user may select one of the control buttons in order to perform a desired action. If the user selects the "snooze" button, the notification may no longer be displayed on the display device, but the notification may be displayed again in a predetermined amount of time (e.g., five or ten minutes). If the user selects the "dismiss" button, the notification may no longer be displayed on the display device, though the notification may persist in the communication thread for that patient, depending on the content in the notification and user preferences.

If the user selects the "go to patient" button, an aspect of the communication channel specific to the patient mentioned in the notification may be displayed. For example, if a user were to select the "go to patient" button of action menu 830 in response to display of notification 820, the communication thread for patient 1234 may be displayed (e.g., communication thread 200 of FIG. 2 or communication thread 700 of FIG. 7), or a dashboard for patient 1234 may be displayed (e.g., dashboard 300 of FIG. 3 or vital signs interface 600 of FIG. 6). As explained above with respect to FIGS. 2-4, the notification may be included in the communication thread and/or on the dashboard, along with other communication occurring on the communication thread and/or along with other relevant patient information on the dashboard. In this way, the user may be presented with the most relevant information pertaining to the patient state. Further, by displaying the communication thread in response to user selection of the "go to patient" button, for example, the user may be able to inform other care providers who are also included on that communication thread of current and/or planned actions, such as notifying the other care providers that the user is en route to the patient, currently administering treatment, etc.

While action menu 830 was described above as being displayed in response to display of notification 820, in some examples action menu 830 may be displayed in response to any notification being displayed, such as in response to notification 800 and/or 810 being displayed.

Thus, one or more patient-specific notifications may be displayed automatically on a display device associated with or used by a care provider monitoring a patient. Further, in some examples, similar notifications may be displayed on display devices associated with or used by other care providers also monitoring the patient. The notifications alert the care provider(s) to changes in patient state or other relevant information relating to care of the patient. The notifications may be generated by a virtual healthcare assistant. The notifications (or a displayed menu associated with the notification) may be selectable to launch a communication thread that displays communication between the care providers monitoring the patient and a virtual healthcare assistant, and the communication thread includes medical information of the patient. The notifications, along with other communication relating to the patient, may be seen within the communication thread. For example, referring to FIG. 8A, the notification may include a menu including a button that, when selected, launches a communication thread, such as the communication thread illustrated in FIG. 11 and described in more detail below. The communication thread includes the notifications, and thus the notifications are also displayed via the communication thread.

In this way, the computing device provides a specific manner of displaying a limited set of information (e.g., the notifications, which may then be selected to launch the communication thread) to the user, rather than using conventional user interface methods to display a generic index/list on a computer that may require the user to step through multiple menus and/or lists of communications and alerts to find the relevant medical information. The notification-communication thread interface link disclosed herein may be advantageous because it avoids a user having to scroll around and switch views multiple times to find desired data/functionality, thereby preventing drilling down through many layers to get the desired data/functionality which may be slow, complex, and difficult to learn. The disclosed notification-communication thread interface link may improve the efficiency of using the computing device by bringing together the medical information most relevant to the user (via the notifications) and the communication thread referencing the medical information, allowing the user to view the most relevant medical information discussed on the communication thread without actually accessing an electronic medical record or separate interface where patient monitoring data may be displayed. The speed of a user's navigation through various views and windows may be improved because the disclosed link between the communication thread and notifications saves the user from navigating to an electronic medical record database, opening the database up, and then navigating within the database to enable the medical information of interest to be seen or a function of interest to be activated.

Such a configuration may be particularly advantageous for care providers that may be monitoring/attending to multiple patients at one time. For example, a physician in a hospital may oversee care of multiple patients, requiring the physician to frequently change location (e.g., between hospital rooms) to provide care to all patients. If the physician has access to a computing/display device at each different location, the physician may be notified, via the notifications described herein, if a patient in a different location (e.g., different room) than where the physician is currently located is undergoing a change in status that requires attention from the physician. By providing the notification-communication thread link as described above, the physician may be able to launch the appropriate communication thread directly from the notification, which may prevent the physician from navigating through multiple layers of menus and interfaces to reach the relevant medical information for that patient and preventing the physician from erroneously accessing medical information from the wrong patient. Further, by providing a direct link to the communication thread, the physician may be able to view the care status of the other care providers also monitoring the patient, which may reduce redundant or unnecessary care. For example, upon receiving a notification that a patient status has changed, potentially requiring action on the part of a care provider, the physician may launch the communication thread from the notification and be informed, via the communication thread, that another care provider is already in the room with the patient and commencing treatment of the patient. This may allow the physician to stay in his or her current location and continue attending to other patients. Conversely, if the physician sees, via the communication thread, that care of the patient has not commenced, the physician may notify the other care providers that the physician is going to the patient to administer treatment/monitoring.

FIG. 9 shows an example notification settings page 900 that may be displayed on a display device, such as display device 602. Notifications settings page 900 may be displayed in response to a request from a user, such as in response to a user selection of a menu item or other selection. Via notifications settings page 900, a user may be able to set preferences for how notifications output via collaborative space server system 102 will be received, displayed, and treated for the computing/display device used by that user (e.g. for display device 602). Computing/display devices used by other users may have at least some different notification settings.

As shown in FIG. 9, notifications settings page 900 includes six sections of information and settings—a guide to notifications section 910, a patient status changes section 920, a patient parameter updates section 930, a messages and callouts section 940, a virtual healthcare assistant actions section 950 (referred to as "Alan actions" in FIG. 9), and a general information section 960. The guide to notifications section 910 may present various information relating to notifications to a user of display device 602, including a button that may present information relating to how the virtual healthcare assistant/collaborative space server system 102 utilizes notifications (e.g., "how Alan uses notifications") and a button that may present information relating to the different notification levels (e.g., "notification levels"). If selected, the information relating to the different notification levels button may cause an explanation of each notification importance level to be displayed (e.g., none, low, medium, high). Further, in some embodiments, via the notification levels button, the user may be presented with an interface where the user may select preferences for each notification level, such as whether notifications of each level will be displayed if the display device is asleep, if haptic and/or audio feedback is output along with display of the notifications of that level, if the user is allowed to dismiss notifications of that level, etc.

The patient status changes section 920 may allow a user to adjust the classification/level of various patient status changes, including a patient shifting to a stable condition, a patient shifting to a warning condition, a patient shifting to a critical condition, a patient being discharged from the medical facility, and a patient moving off the current unit. As shown in FIG. 9, the current settings for display device 602 (which is operably coupled to a computing device that may handle aspects of the notifications and/or which may transmit the notifications settings to the collaborative space server system 102, such as care provider device 134) are set such that green conditions (e.g., patient shifting to stable) are given low importance, yellow conditions (e.g., patient shifting to warning) are given medium importance, red conditions (e.g., patient shifting to critical) are given high importance, a patient being discharged is given medium importance, and a patient being moved off unit is given low importance. Each of these settings may be adjusted by the user, other than the patient shifting to a critical condition. Due to the time-sensitive nature and importance of actions occurring if a patient shifts to critical condition, the administrator of the collaborative healthcare system may want to ensure that all end users, such as care providers, cannot shut off or minimize these notifications, and thus may dictate how the critical condition notifications are received and handled. The user may be able to adjust the importance level of each of the remaining categories of patient status changes.

Likewise, the user may adjust the level of importance for the notifications related to the categories within the patient parameter updates section 930, including when a patient parameter has been updated (herein, set as low importance) and when a patient parameter has passed a limit (herein, set as medium importance). Further, the user may be able to adjust which patient parameters, if updated, may trigger a notification and/or the user may be able to adjust the limits for the various patient parameters.

For the messages and callouts section 940, the user may be able to adjust the level of importance for notifications related to callouts in a patient channel (e.g., when the user is mentioned in a communication thread, herein set as low importance) and direct messages (herein set as low importance). The VHA actions section 950 (e.g., Alan actions, when the VHAs are given a human persona) may include notifications related to reminders from the VHA and updates from the EMR, each of which may be set to a level by the user (as shown, reminders are set to low importance and updates from EMR are set to medium importance). The general information section 960 may include notifications related to healthcare practitioner status changes (e.g., when a care provider starts or stops providing care for a patient) and new patients being added, each of which have been set to no notifications.

It is to be understood that the notifications settings page 900 is exemplary, and other configurations are possible. For example, rather than (or in addition to) making updates to notifications preferences via notifications settings page 900, a user may update notification settings via a communication thread, as will be explained in more detail below. Further, in some examples, rather than allowing a user to set each notification setting individually (other than the critical condition notifications), the collaborative space server system 102 may automatically set some or all notification settings based on the healthcare role provided by the user. For example, a lead physician may have different notification settings than a nursing assistant, due to the different roles and different numbers/types of patients seen by the different care providers.

Figure 10:
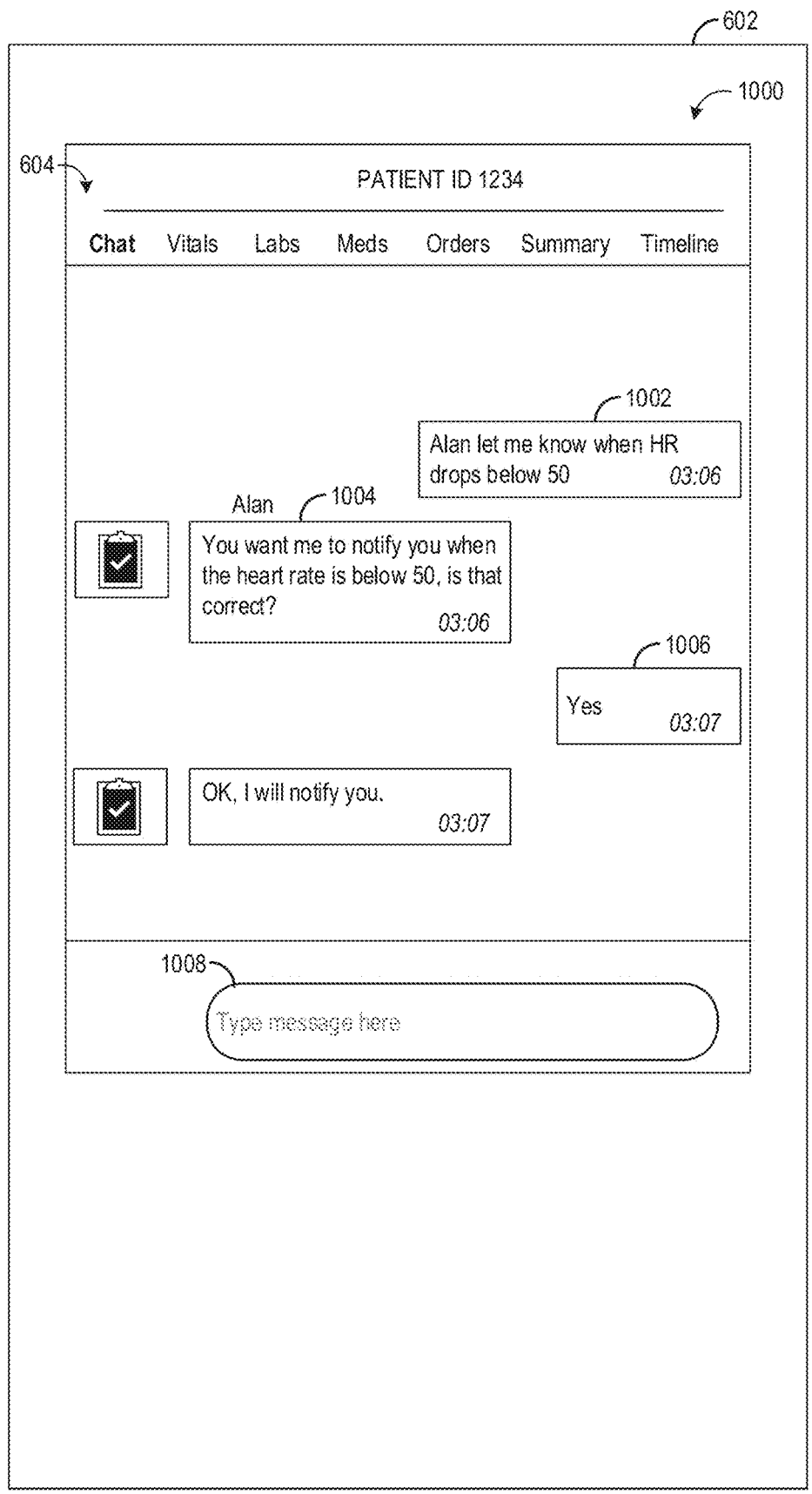
FIGS. 10-12 show an example display device displaying examples of communication threads occurring on a communication channel of the collaborative healthcare system.

FIG. 10 shows a communication thread 1000 of a patient-specific communication channel, and as such may be a non-limiting example of communication thread 104 introduced in FIG. 1. Communication thread 1000 may be displayed on the display device 602. Communication thread 1000 may be displayed in response to a user request to display the communication thread (e.g., by selecting the "chat" tab) and may include the identification header 604 that identifies the patient being discussed/monitored via the communication thread. In the illustrated example, communication thread 1000 is specific to patient ID 1234. In the illustrated portion of communication thread 700, communication is occurring between a care provider (e.g., Dr. Smith) and a virtual healthcare assistant ("Alan"). Communication thread 1000 is being viewed by Dr. Smith, although any authenticated/approved user may view communication thread 1000.

As shown by the first message 1002, Dr. Smith enters a request to be notified when the heart rate of patient 1234 drops below a threshold heart rate (e.g., "Alan let me know when HR drops below 50"). The request is entered via text or voice as a natural language input, e.g., the request is conversational in nature and does not include search terms entered into search fields. The request is also directed at the virtual assistant, as the request starts with the virtual assistant's "name," Alan. The virtual assistant then processes the natural language input to determine that the natural language input includes a user request to receive a notification when the patient heart rate drops below 50, where the notification is specific to patient 1234 and specific to Dr. Smith. To ensure accuracy in the updated notification settings, Alan then outputs a second message 1004 into the communication thread requesting confirmation of the received personalized notification setting. After Dr. Smith confirms (e.g., via third message 1006), the virtual healthcare assistant may then update its notifications settings so that Dr. Smith (or rather, a computing/display device registered as being used by Dr. Smith) is sent a notification any time patient 1234's heart rate drops below 50.

FIG. 10 also shows a message box 1008 via which a user (e.g., Dr. Smith) may enter messages into communication thread 1000. For example, the user may enter text into message box 1008 using a keyboard, a touch screen, or voice input. The text may be natural language text that may be parsed by Alan to determine if the user has entered a request for information, a personalized notification setting, or other information. Further, all messages entered into communication thread 1000 may be viewed by all other care providers joined to the communication thread 1000, as explained above.

While communication thread 1000 includes an example of a personalized notification setting (e.g., where Dr. Smith requested to be notified of a change in a parameter of patient 1234), in some examples the notification request may be global, such that all care providers joined to communication thread 1000 or otherwise providing care to patient 1234 may receive a notification when the specified parameter reaches the specified limit (e.g., when heart rate drops below 50). For example, to make a global request, Dr. Smith may send a message that states "Alan let us know when HR drops below 50," and in response, the virtual healthcare assistant may then update its notifications settings so that all care providers joined to communication thread 1000 are sent a notification any time patient 1234's heart rate drops below 50.

Figure 11:
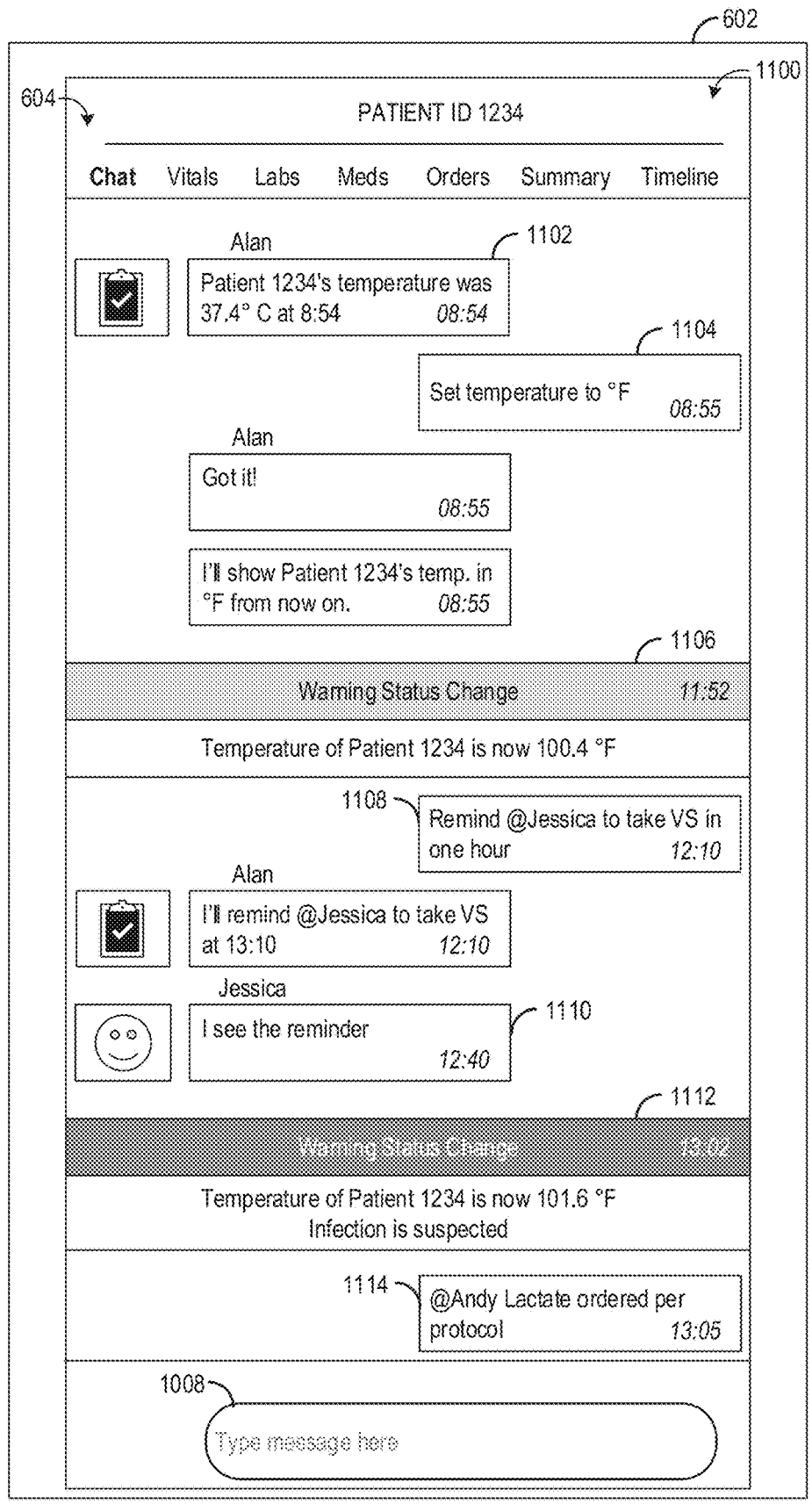

FIG. 11 shows another example communication thread 1100 of a patient-specific communication channel, and as such may be a non-limiting example of communication thread 104 introduced in FIG. 1. Communication thread 1100 may be displayed on the display device 602. Communication thread 1100 may be displayed in response to a user request to display the communication thread (e.g., via selection of the chat tab) and may include the identification header 604 that identifies the patient being discussed/monitored via the communication thread. In the illustrated example, communication thread 1100 is specific to patient ID 1234. In the illustrated portion of communication thread 1100, communication is occurring between a first care provider (e.g., Dr. Smith) and the virtual healthcare assistant ("Alan") as well as a second care provider ("Jessica"). Communication thread 1100 is being viewed by Dr. Smith, although any authenticated/approved user may view communication thread 1100.

Communication thread 1100 commences with a first message 1102. First message 1102 is sent by Alan and includes an update on a temperature of patient 1234. Similar to communication thread 1000, communication thread 1100 includes a request from Dr. Smith to update personalized notifications. For example, Dr. Smith sends a second message 1104 requesting that all temperature measurements be in degrees Fahrenheit rather than Celsius.

Communication thread 1100 also includes a first notification banner 1106. First notification banner 1106 represents a notification generated and output by the virtual healthcare assistant in response to a patient status change, herein that patient 1234's temperature has increased above a first threshold temperature (e.g., above 100° F.). Such a temperature increase changes the condition of patient 1234 from stable to warning, and hence the banner includes a portion that may indicate the status change (e.g., the top portion of the banner may be yellow). Thus, a notification generated and output by a virtual healthcare assistant in response to a change in patient status may be output as a pop-up element (as shown in FIG. 8B, for example) and as a banner in a communication thread for the patient. The first notification banner 1106 may be inserted in communication thread chronologically, such that it appears in the thread at a position that corresponds to the time the notification was first generated.

Communication thread 1100 includes a third message 1108 where Dr. Smith enters a request for a personalized notification, and specifically a request for a reminder to be generated. Therein, Dr. Smith requests that Alan remind Jessica to take the vital signs for patient 1234 in one hour. As explained above with respect to FIG. 9, when a care provider is called out/mentioned in a message on a communication thread, that care provider may receive a notification of the callout. Accordingly, while not shown in FIG. 11, Alan may output a notification to a computing/display device registered to Jessica (or that Jessica is known to interact with) that notifies Jessica that she was called out by Dr. Smith on the communication thread for patient 1234. This may allow Jessica to navigate to the communication thread (e.g., by selecting the "go to patient" button associated with the notification) in order to view the callout, and also to acknowledge the callout. Thus, as shown by fourth message 1100, Jessica acknowledges the reminder. The virtual healthcare assistant may then send a reminder to Jessica (and only to Jessica and not any other care providers) at the appointed time to take the vital signs for patient 1234. As an example, a notification similar to the notification illustrated in FIG. 8A may be sent to Jessica.

A second notification banner 1112 is inserted in the communication thread 1100, indicating that a second notification was issued alerting the care providers that the status of patient 1234 has changed to critical due to the patient's temperature reaching or exceeding a second, higher threshold temperature (e.g., 101.5° F.). The second notification banner 1112 is inserted at the time that the second notification is first generated, and placed into the thread in chronological order. The second notification banner 1112 includes a portion that may indicate the status change (e.g., the top portion of the banner may be red to indicate the critical condition of the patient). Further, the virtual healthcare assistant may output a prediction of a medical condition of the patient based on the patient's increase in temperature (and based on other patient vital signs, medical history, etc.) as part of the notification, which in the current example includes suspicion of infection.

In response to the status of the patient changing to critical, the care providers may desire to gather further information on the patient's state and/or commence treatment to stabilize the patient. As the patient may have multiple care providers that may be located in different areas of the medical facility (e.g., attending to other patients), responding to the patient status change may require coordination to ensure proper assessment and treatment is carried out while not unduly sacrificing care of other patients. The communication thread may facilitate this coordination by allowing a mechanism for the different care providers to quickly communicate with each other and assess current patient state, treatment plan, etc. To this end, Dr. Smith notifies the other care providers, and in particular another care provider (Andy) of interest who is also attending to patient 1234, that assessment of sepsis for patient 1234 has started, by sending a fifth message 1114 on the communication thread 1100. The fifth message 1114 calls out Andy to notify Andy (and any other care providers currently communicating on communication thread 1100) that a lactate test has been ordered per the sepsis protocol. In this way, a notification may be sent to Andy alerting Andy that he has been mentioned in the communication thread for patient 1234, which may be in addition to the notification sent alerting Andy (and the other care providers attending to patient 1234) to the change in patient status. In this way, Andy and the other care providers may be notified of not only the change in patient status, but also alerted of the current patient assessment/treatment status. As an example, a computing/display device registered and/or used by Andy may be sent a notification similar to the notification illustrated in FIG. 8C. By selecting the "go to patient" button, communication thread 1100 may then be displayed on the computing/display device registered and/or used by Andy, so that Andy may view the callout by Dr. Smith in context of the most recent patient medical events.

The communication threads described herein may provide a further mechanism via which a user may interact with the communication thread, beyond the message box 1008. As shown by communication thread 1200 of FIG. 12 (which is a continuation of communication thread 1100 and thus includes fifth message 1114), a user (e.g., Dr. Smith in the example presented in FIG. 12) may select a desired message on the communication thread, which may cause a message action menu 1202 to be displayed. For example, the user may enter a single or double click or touch input on fifth message 1114, which may trigger display of message action menu 1202. Message action menu 1202 may include various control buttons that may cause different actions when selected. As shown, message action menu 1202 includes a reply button, a bookmark button, and a copy button. When the reply button is selected, a message box may be displayed (or the active cursor may be moved to an already displayed message box, such as message box 1008), which may allow the user to enter text or voice input that may be sent as a message on the communication thread (e.g., visible to all care providers joined to the communication thread) or sent as a direct message to a selected care provider (for example, if a message sent by another care provider is selected and the reply button is then selected, a direct message to that care provider may be sent). When the copy button is selected, the text in the selected message may be copied onto the computing/display device's clipboard for later pasting into a desired area (e.g., a message box in the communication thread or other location).

Figure 12:
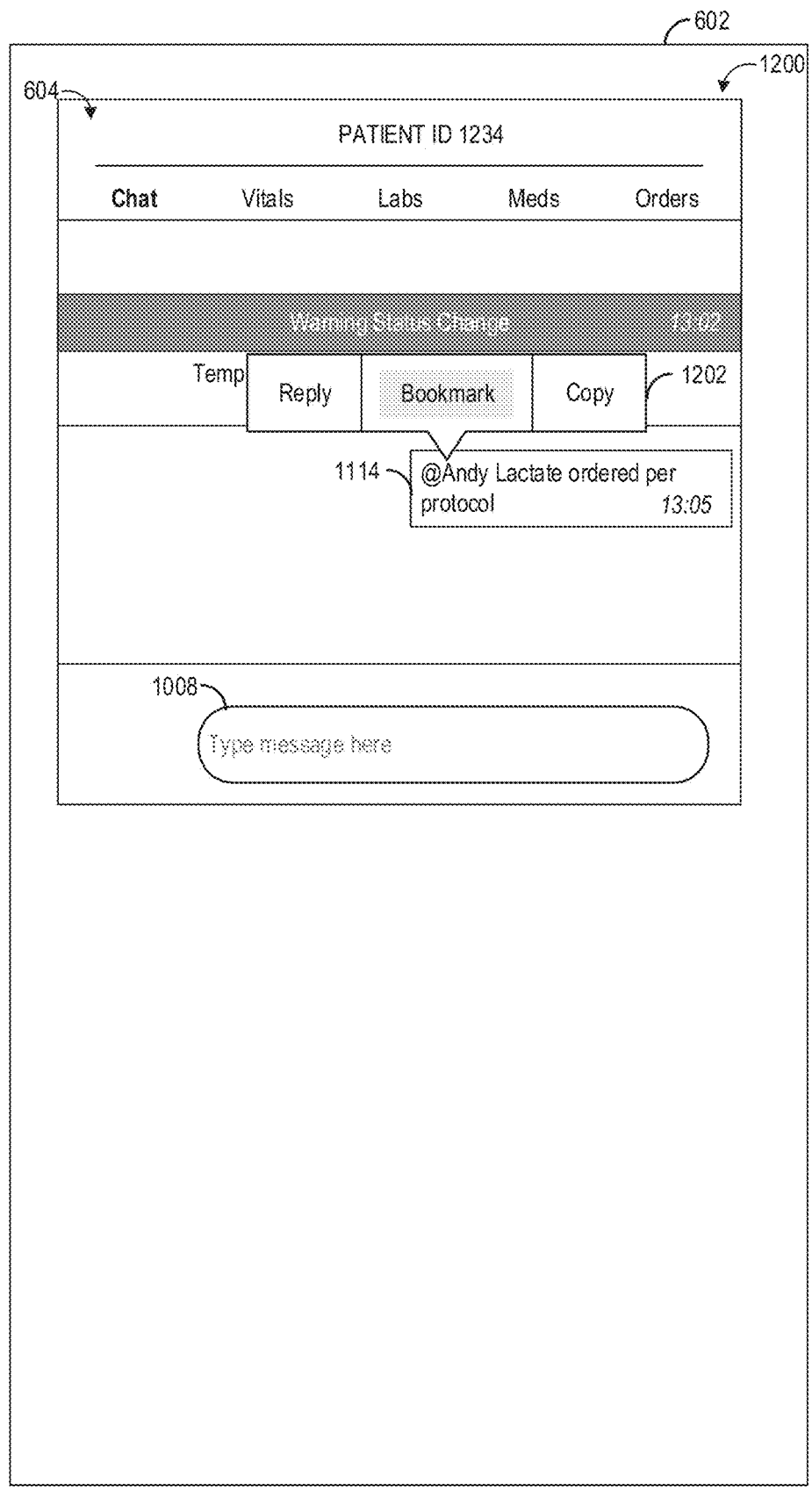
Figure 13:
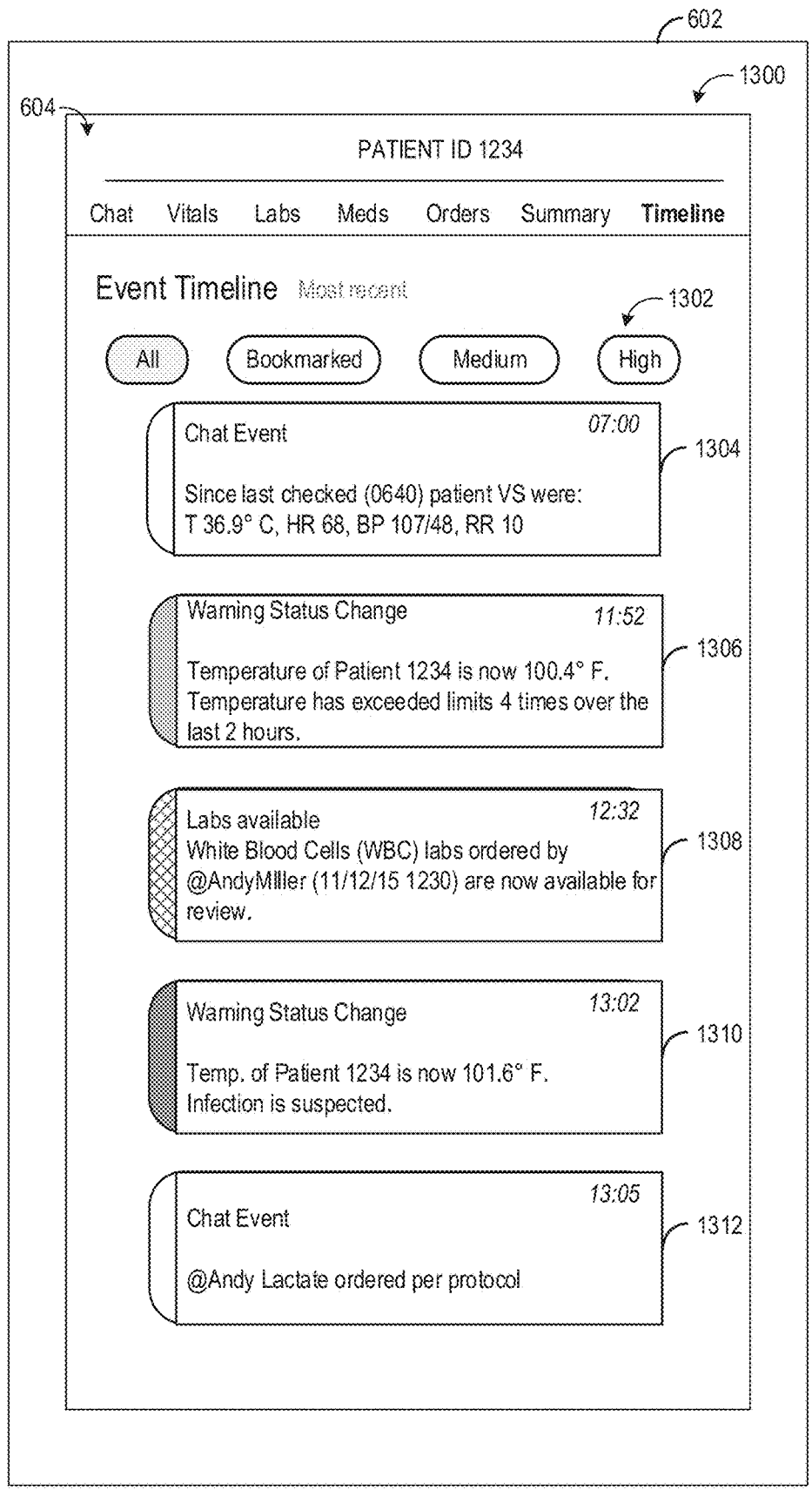
FIG. 13 shows an example display device displaying an example timeline that may be output via a communication channel of the collaborative healthcare system.

When the bookmark button is selected (as shown in FIG. 12), the associated message from the communication thread (e.g., fifth message 1114) may be saved into a timeline for the patient. As explained previously, the timeline may include patient medical information that was generated over a prior period of time, such as the last 8 or 12 hours. The timeline may present a brief distillation of current patient status to facilitate quick and seamless transfer of patient care from one care provider to another during a shift change, for example. The patient medical information included in the timeline may include some or all notifications generated by the virtual healthcare assistant during the prior time period, some or all ordered lab tests and/or received lab test results, some or all ordered or administered treatments or medicines, and some or all messages on the communication thread for that patient over the prior time period. The messages included in the timeline may be selected by the care providers via the communication thread, by selecting the bookmark button as shown in FIG. 12. In other examples, a care provider may select a message for inclusion in the timeline via voice input or other suitable input.

FIG. 13 shows an example timeline 1300 of a patient-specific communication channel. Timeline 1300 may be displayed on the display device 602. Timeline 1300 may be displayed in response to a user request to display the timeline (e.g., via selection of the timeline tab of the identification header 604) and may include the identification header 604 that identifies the patient being discussed/monitored via the communication thread. In the illustrated example, timeline 1300 is specific to patient ID 1234. Timeline 1300 is being viewed by Dr. Smith, although any authenticated/approved user may view timeline 1300.

The information included in timeline 1300 may be filtered in a suitable manner to assist a user in navigating through the information included in the timeline. Accordingly, a plurality of filtering buttons 1302 are included in timeline 1300. The plurality of filtering buttons 1302 includes an all information button ("All"), which when selected (as shown in FIG. 13) causes display of all pieces of information included in the timeline. The plurality of filtering buttons 1302 further includes a bookmarked information button ("Bookmarked"), which when selected causes display of only the bookmarked/selected messages from the patient communication thread. The plurality of filtering buttons 1302 additionally includes a medium notifications button ("Medium") and a high notifications button ("High"), which when selected cause display of only medium level notifications related to the patient or only high level notifications related to the patient, respectively.

Because the all information button has been selected, all pieces of information designated to be included in timeline 1300 are displayed on display device 602. The pieces of information include a first chat event 1304, a first notification 1306, a lab test result notification 1308, a second notification 1310, and a second chat event 1312. The first chat event 1304 is a message sent by the virtual healthcare assistant at 07:00 that day and includes patient vital signs taken prior just prior to 07:00. The first message 1304 may be included in timeline 1300 due to one of the care providers joined to the communication thread for patient 1234 selecting the message from the communication thread (e.g., by selecting third message 706 of communication thread 700 of FIG. 7).

The first notification 1306 is the notification that the patient status has changed to warning due to the temperature of patient 1234 exceeding a first threshold, which was also included in communication thread 1100 of FIG. 11 as first notification banner 1106. The first notification 1306 may be included in the timeline 1300 automatically. For example, all medium and high level notifications may be included in the corresponding timeline automatically (e.g., without explicit input on the part of a user). The lab test result notification 1308 indicates that results for a lab test ordered for patient 1234 (e.g., white blood cell analysis) are available to view. The lab test result notification 1308 may also be included in the timeline automatically. For example, any lab test results, when made available, may be automatically inserted into a corresponding timeline.

The second notification 1310 is the notification that the patient status has changed to critical due to the temperature of patient 1234 exceeding a second threshold, which was also included in communication thread 1100 of FIG. 11 as second notification banner 1112. The second notification 1310 may be included in the timeline 1300 automatically. The second chat event 1312 is a message sent by a care provider (Dr. Smith) at 13:05 that day and an indication that a lactate test was ordered for patient 1234. The second message 1312 may be included in timeline 1300 due to one of the care providers joined to the communication thread for patient 1234 (e.g., Dr. Smith) selecting the message from the communication thread (e.g., by selecting fifth message 1114 of communication thread 1100 and 1200 of FIGS. 11 and 12, as shown by selection of the bookmark button of FIG. 12).

In some examples, while viewing timeline 1300, a user may select an event or notification included in timeline 1300 (e.g., by entering a touch input to the display device at the desired event or notification), which may trigger display of additional information relevant to that event or notification. For example, if first chat event 1304 is selected, the communication thread for that patient, at the time of the first chat event, may be displayed. Likewise, selection of a status change notification may cause display of the communication thread where the notification banner for that status notification is included, or it may cause display of a patient dashboard (such as the vitals interface shown in FIG. 6 or the dashboard shown in FIGS. 3 and 4), where additional patient medical information may be viewed. Selection of the lab test result notification 1308 may cause display of a lab interface, where the results for the particular lab test may be viewed.

In this way, handover between shifts may be facilitated with a timeline. The information included in the timeline may include medium and high level notifications and/or any message in a communication thread that was either sent by a virtual healthcare assistant or by one of the care providers that was chosen to be included in the timeline. While not shown in FIG. 13, the messages included in the timeline may include graphs and/or other medical data where appropriate. Selecting a message to be included in the timeline may be performed by any one of the care providers. The timeline then presents a single view of the patient's status in the last shift. To this end, the timeline may only include events, notifications, and/or messages that were generated and/or obtained over a prior predetermined amount of time. For example, all the information in a current timeline may have been generated and/or obtained over the prior 12 hours. As time progresses, outdated events, notifications, and/or messages may be automatically removed from the timeline. In other embodiments, all events, notifications, and/or messages included in the timeline may be kept in the timeline, even as time progresses beyond the predetermined amount of time. In such examples, the events, notifications, and/or messages generated and/or obtained over the prior predetermined amount of time may be preferentially displayed, and then the outdated events, notifications, and/or messages may be viewed, if desired, for example by scrolling to the outdated messages.

FIG. 14 is a flow chart illustrating a method 1400 for a collaborative healthcare system serving a medical facility, such as a hospital. Method 1400 may be executed by a processor of a computing device (such as processor(s) 132 of server system 102 of FIG. 1) according to instructions stored on a non-transitory memory of the device (e.g., memory 130 shown in FIG. 1) in combination with the various signals received at the server system from components of the collaborative healthcare system (e.g., patient medical data signals from monitoring devices 120, communication from hospital operational systems 118, etc.) and signals sent from the server system to the care provider devices and/or other system components.

At 1402, method 1400 includes receiving a notification that a patient has been admitted to the medical facility. The notification may be received from the hospital operational systems, and may include a patient identifier, patient state (e.g., the condition for which the patient is being admitted), and care provider information. The care provider information may include identifiers of various care providers (such as doctors and nurses) that are currently attending to the patient.

At 1404, method 1400 includes generating a communication channel including a communication thread and a dashboard for the patient. In order to generate the communication channel, verified care providers of the patient (e.g., as indicated by the notification from the hospital operational systems) and one or more virtual healthcare assistants (VHAs) may be joined to the communication channel, as indicated at 1406. The communication channel may facilitate text and/or rich-media based messages to be sent among all the verified care providers and VHAs that are joined to the communication channel. The one or more VHAs may include an EMR VHA, a guideline VHA, a predictive VHA, a listening VHA, a monitoring VHA and/or other VHAs. To join the channel, each VHA may receive a message that a new channel has been opened and the access application (e.g., executing on the server system 102) may add the VHAs to the eligible participants of the channel. Moreover, in some examples, not all available VHAs may be invited to all channels (e.g., a sepsis VHA may not be invited in a non-relevant case or the listening VHA may not be invited due to patient refusal to be monitored by recording).

Generating the dashboard may include configuring the dashboard based on the patient state and/or user settings, as indicated at 1408. As explained previously, a patient dashboard may be a graphical user interface that facilitates display of patient medical information, such as real-time vital signs, medical history, treatment plan, and/or other information. The dashboard may also include relevant/desired messages from the communication thread. Which medical information to display on the dashboard and in what format may be determined based on the patient state (e.g., current medical condition for which the patient is being treated) and/or on user settings, which may be configured by the end-viewer of the dashboard. In this manner, different patients may have different medical information displayed on different dashboards, and different care providers may view different medical information for the same patient, if desired.

At 1410, method 1400 includes receiving text- and/or rich-media-based messages from the participants on the communication channel, including care providers and VHAs. During the course of patient care, care providers may communicate with each other on the communication channel via messages of the communication thread to coordinate care, give care instructions, and/or confirm appropriate care is being carried out. Further, care providers may send requests to the VHAs via the communication thread for various information related to the patient care, including patient medical history, care guidelines, predicted future patient state, recommended lab tests, etc. Further still, VHAs may send notifications via the communication thread of changes in patient state, patient medical history, patient care guidelines, predicted future patient states, lab test status, etc. The messages sent from a care provider may be sent from a care provider device (e.g., device 134) and received at the server system via a suitable connection (e.g., wired or wireless, such as via the Internet). The messages sent from the VHAs may be generated by the VHAs, which may be stored and executed on the server system, the cloud, and/or a remote device. As used herein, messages may refer to any suitable information sent and received on the communication thread, including but not limited to text messages (entered via typing, touch, or stylus input, voice input, or automatically generated by a VHA), images, voice messages (e.g., recordings of voice input), and videos.

At 1412, method 1400 includes distributing the received messages to other participants on the communication channel and saving the received messages as a communication thread. Each message that is sent to the server system may be tagged with various identifiers that identify the sender as well as the patient communication thread to which the message pertains (e.g., the patient identifier). The server system may then send the message to other participants of the communication channel, e.g., the care providers and/or VHAs that did not send the original message, and save the message as part of a saved communication thread. The saved communication thread may then be viewed by other users at other times, retrieved in response to a user request to view some or all of the communication thread, etc. However, in some examples, the device from which the original message was sent (e.g., the care provider device) may send the message to all other participants on the communication channel, and thus the server system may not distribute the message to the other participants.

At 1414, method 1400 includes receiving patient medical information. The patient medical information may be received from one or more patient monitoring devices that are configured to measure patient state and condition, including sensors that measure vital signs (e.g., blood pressure, heart rate, and blood oxygen level), diagnostic imaging modalities, microphones in proximity to the patient, and so forth. Additionally, the patient medical information may be received from the communication thread. For example, two care providers may be messaging each other on the communication thread and exchanging information relating to the patient, such as visual information (e.g., skin pallor, redness, or yellowness) of the patient that may indicative of patient state. One or more of the VHAs may be configured to parse the message and determine that relevant medical information is being exchanged and then save the medical information as messages within the communication thread.

At 1416, method 1400 includes updating a digital twin of the patient with the medical information. The digital twin may be a digital replica/representation of the patient that is saved at the computing device (e.g., digital twin 108 saved on the server system 102). The digital twin may include patient demographic information, medical history, and other information to provide, to the extent possible, a simulation/representation of the current patient medical state. When new or updated medical information is received, the digital twin may be updated to reflect the most recent patient medical state. The digital twin may be accessed (e.g., by one or more of the VHAs) to retrieve patient medical information, predict future patient states (e.g., simulations may be performed using the information stored in the digital twin to determine the probability of the patient developing a certain condition), identify the most relevant lab tests to be conducted to diagnose a patient condition, and provide appropriate context when retrieving care guidelines.

At 1418, method 1400 includes outputting the communication thread for display when prompted. In an example, the prompt may include an explicit request to view the communication thread for the patient, entered by selection of an appropriate link/control button on the patient dashboard or selection of the patient's communication thread from a collaborative interface, as indicated at 1420. For example, a message button may be displayed via the patient dashboard, and selection of the message button may trigger display of the communication thread for that patient. In another example, a patient link may be selected to launch the communication thread from a collaborative system interface. In an example, the communication thread may be output for display automatically in response to a request from one or more of the VHAs, as indicated at 1422. For example, a listening VHA may detect that one or more care providers are discussing a particular piece of the patient's medical history, and the listening VHA may send a portion of the communication thread that includes reference to the particular piece of medical history to the care provider's device for display. In another example, a VHA may detect that a patient vital sign has reached a level that may indicate a potential urgent patient condition and the VHA may output an alert regarding the vital sign on the communication channel. In some examples, issue of such an alert may prompt automatic display of the communication thread on each participant's display device.

At 1424, method 1400 includes outputting the dashboard for display when prompted. In an example, the prompt may include an explicit request to view the dashboard for the patient, entered by selection of an appropriate link/control button on the communication thread or selection of the patient's dashboard from a collaborative interface, as indicated at 1026. For example, as shown in FIG. 2, a link to the dashboard may be displayed in the communication thread, and selecting the link may trigger display of the dashboard for that patient. In an example, the dashboard may be output for display automatically in response to a request from one or more of the VHAs, as indicated at 1428. For example, the listening VHA may detect that a care provider is discussing the patient's current medical state and may automatically output the dashboard for display on the care provider's device so that the care provider may view patient medical information displayed in the dashboard that relates to the current medical state being discussed. Method 1400 then returns.

Figure 15:
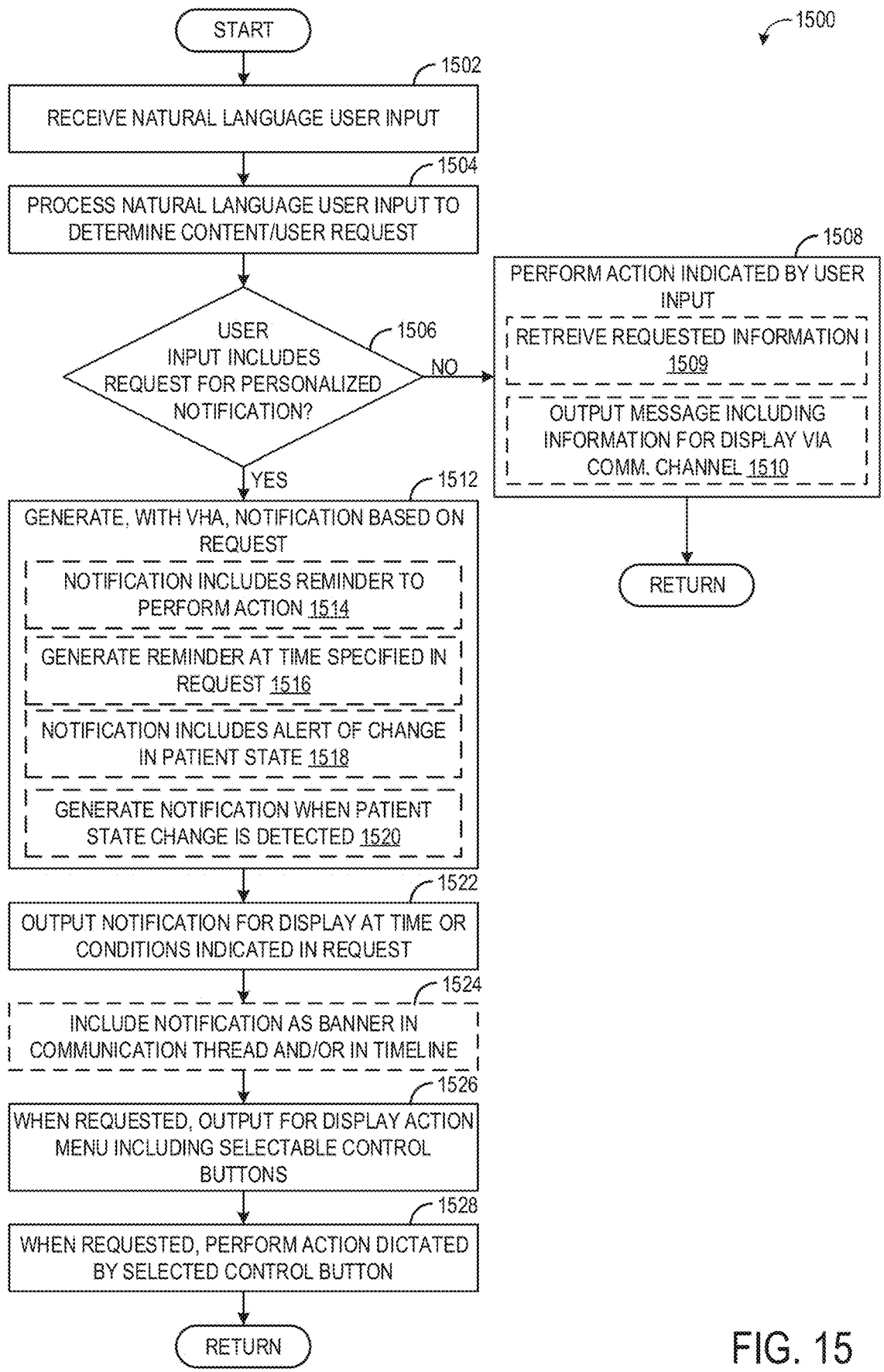
FIGS. 15 and 16 are flow charts illustrating example methods for generating and outputting notifications via the collaborative healthcare system.

FIG. 15 is a flow chart illustrating a method 1500 for generating personalized notifications via a virtual healthcare assistant that are then output to a care provider. Method 1500 may be executed by a processor of a computing device (such as processor(s) 132 of server system 102 of FIG. 1) according to instructions stored on a non-transitory memory of the device (e.g., memory 130 shown in FIG. 1). As explained above with respect to FIG. 1, the server system 102 may store/execute one or more virtual healthcare assistants (VHAs) that are configured to perform certain tasks related to providing medical information of the patient to the one or more care providers attending to the patient, as explained below.

At 1502, method 1500 includes receiving a natural language user input. The natural language user input may be input as a message from a care provider, via voice or text, and may include patient-specific information in natural language form. For example, as explained previously, each patient may have a dedicated communication channel including a communication thread that facilitates communication among the care providers treating the patient and one or more VHAs. When a care provider enters a natural language input on the communication thread, the input (e.g., message) may be received at the server system and the input may be processed, via the one or more VHAs, to determine the content of the natural language user input, as indicated at 1504. The one or more VHAs may utilize a speech recognition engine in examples where the natural user input is input via voice. As explained previously, the one or more VHAs may be trained to process natural language inputs to determine the content of the input, e.g., determine if the input includes a request for information, and if the content incudes a request for information, the one or more VHAs may be trained to determine which patient the care provider is referring to and what information is being requested. In some examples, each VHA may process a received message to understand (in natural language) the intent of the message and determine if the intent of the message includes a task that the VHA is trained/configured to perform. In some examples, the server system may include a central entity configured to understand the intent of the message (e.g., from the natural language of the message) and determine which VHA is best configured to handle the request. Then, the mapping from intent (and VHAs) to a specific API of a specific VHA is one-to-one, e.g., only one VHA handles a specific intent (or intent-entity combination).

The information request may be an explicit request, where the care provider explicitly asks for certain medical information, such as "please send me the patient's heart rate over the last four hours." In other examples, the request may be implicit. Implicit requests may include assumptions (on the part of the VHAs executing on the server system) that certain medical information may be helpful, such as when a change in patient vital signs is detected, that are not accompanied by an actual request by the care provider.

At 1506, method 1500 determines if the user input includes a request for a personalized notification to be set. As explained above with respect to FIGS. 10 and 11, a care provider may enter one or more natural language user inputs (e.g., messages on the communication thread) requesting to be reminded to perform a task (e.g., take vital signs, order a lab test, etc.), to be notified if a patient condition changes (e.g., if a patient heart rate drops below a certain threshold, such as 50), or other notification that is not already set. If the user input does not include a request for to set a personalized notification, for example if the user input includes a request to view a data set (e.g., a heart rate trend), a request for treatment guidelines or diagnosis guidelines, or if the user input is not directed at the VHA (e.g., the message is intended for another care provider), method 1500 proceeds to 1508 and performs one or more actions as indicated by the user input. For example, if the user input includes a request for a medical information from the patient's EMR, the VHA (e.g., EMR VHA) may retrieve the information from the patient's EMR and output the information as a message in the communication thread. Thus, in some examples, performing the one or more actions may include retrieving the requested information, as indicated at 1509, and outputting a message including the information for display via the communication channel, as indicated at 1510. In other examples, the one or more actions may simply include saving/distributing the message (e.g., when the user input does not include any requests for information).

If the user input does include a request to set a personalized notification, method 1500 proceeds to 1512 to generate, with a VHA, a notification based on the request. The notification may be generated and then stored for later distribution at the time of the request, or the notification may be generated at the time that the notification is to be sent to the care provider. In some examples, as indicated at 1514, generating the notification may include generating a notification that includes a reminder to perform an action. As explained above, the reminder may include a reminder to take patient vital signs, to order a lab test or administer medication, or to perform virtually any task related to patient care. The reminder may be specific to the care provider that requested the reminder. In other examples, the reminder may be specific to a care provider other than the care provider who requested the reminder. In still further examples, the reminder may be specific to the virtual healthcare assistant, such as a reminder or request to output information in a specific manner (e.g., temperature in degrees Fahrenheit). The reminder may be generated at a time specified in the request, as indicated at 1516. For example, the request may include a request for a care giver to receive a reminder to measure one or more patient vital signs at a specific time, such as an hour from receipt of the request.

In some examples, as indicated at 1518, generating the notification may include generating a notification that includes an alert of a change in patient state, such as a change in patient status (e.g., from warning to critical) or a change in a patient parameter (e.g., a change in a vital sign, such as a change in blood pressure or heart rate). For example, as discussed above with respect to FIG. 10, a care provider may send a message on a communication thread for a patient requesting to be notified when a parameter of that patient (e.g., heart rate) meets a predetermined condition relative to a threshold (e.g., drops below 50 bpm). In such examples, as indicated at 1520, the notification may be generated when the specified change in patient state is detected. The change in patient state may be detected by one or more VHAs (e.g., EMR VHA 110 and/or monitoring VHA 117) based on patient monitoring data, which may be received from monitoring devices 120, digital twin 108, and/or EMR database 122 of FIG. 1, for example. Additionally, at least in some examples, the notification may be classified as a low, medium, or high level notification based on user settings (e.g., as explained above with respect to FIG. 9), severity of the patient status that triggered the notification, or other parameter.

At 1522, the requested notification is output for display at the time and/or conditions indicated in the request. For example, if the request included a request for a reminder to perform an action at a specific time, the notification including the reminder may be output for display at the specific time. If the request included a request to be notified when a particular patient state changes, the notification may be output for display when the particular change in patient state is detected. The notification may take on a particular form based on the classification level of the notification. For example, low level notifications may include portions in green (e.g., a banner or outline of the notification may be green), while a medium level notification may include portions in yellow and a high level notification may include portions in red. The notification may be output to a suitable display device or devices. Because the notification is personalized, the notification may only be output to a display device used by the care provider who initiated the request, or only output to a display device used by a care provider specified in the request. However, in some examples, the notification may be output to all care providers who are attending to the particular patient, or other identified care provider or providers.

At 1524, method 1500 optionally includes including the notification as a banner in a communication thread and/or including the notification in a timeline. Because the notification generated at 1512 and output at 1522 is personalized and hence specific to one or only a subset of care providers, the notification may not be distributed to all care providers joined to the communication thread for that patient, as doing so may not be desired by the other care providers. However, in some examples, the notification generated at 1512, in addition to being output as a pop-up notification on the display device of the requesting or specified care provider at 1522, may also be included in the communication thread and/or timeline for that patient. For example, if the notification is deemed, after the request to generate the notification, relevant to all care providers (e.g., the request included a request for only the requesting care provider to be notified when patient heart rate drops below 50, but then the requesting care provider decides, after receiving a notification that the patient's heart rate has dropped below 50, that the other care providers may find it relevant), the receiving care provider may request to have the notification included in the communication thread and/or timeline.

At 1526, method 1500 includes outputting for display an action menu including selectable control buttons, when requested by the user. The action menu may be associated with the notification and may be output for display in response to a user input (e.g., selecting the notification). The action menu may include buttons that, when selected, cause different actions to be performed, such as dismissing the notification, setting a snooze for the notification, or triggering display of additional patient information, such as triggering display of the communication thread for that patient. Accordingly, at 1528, method 1500 includes performing the action dictated by the selected control button when requested. For example, if the user selects the "go to patient" button from the action menu, the communication thread for that patient may be displayed. Method 1500 then returns.

While method 1500 was described above as being carried out by processor(s) 132 of server system 102 of FIG. 1 (as an example), it should be understood that at least some of the elements of method 1500 described above may be carried out by processor(s) 132 of server system 102 of FIG. 1 in concert with a care provider device, such as care provider device 134 of FIG. 1. For example, when a notification is output for display (e.g., at 1522 of method 1500), the processor(s) 132 of server system 102 may output at least some of the notification to the care provider device 134, and the care provider device 134 may then process the received notification (e.g., insert the received notification into a notification template stored locally on care provider device) and display the notification. In another example, when the action menu is output for display (e.g., at 1526 of method 1500), the care provider device 134 may output the action menu for display on the care provider device, and then send a notification to the server system 102 of the user selection of a button of the action menu, if needed. For example, if the "go to patient" button is selected so that the communication thread for that patient is displayed on the care provider device, the server system 102 may send the communication thread to the care provider device, or send any messages from the communication thread that have yet to be viewed on the care provider device.

Figure 16:
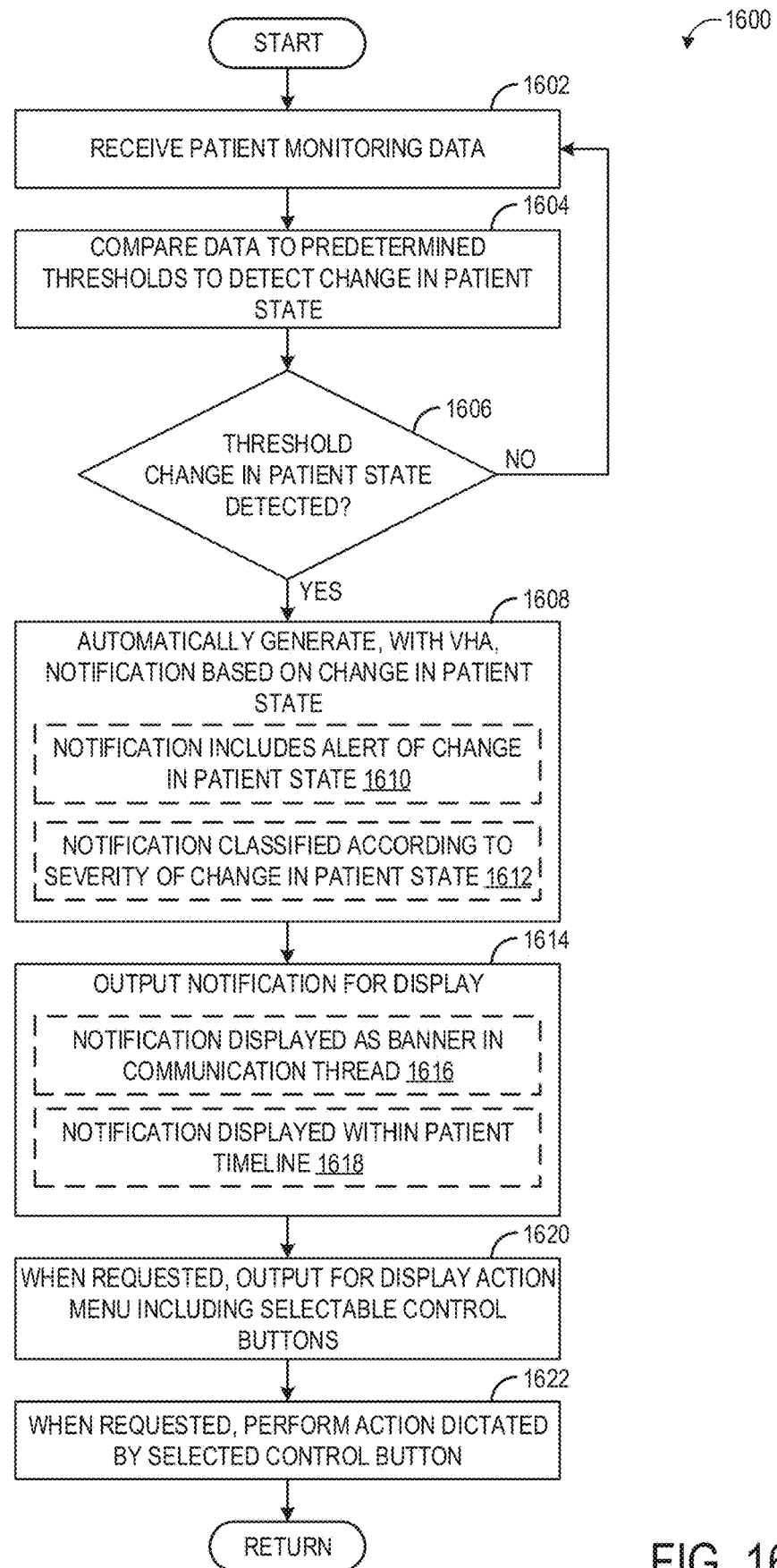
Figure 17:
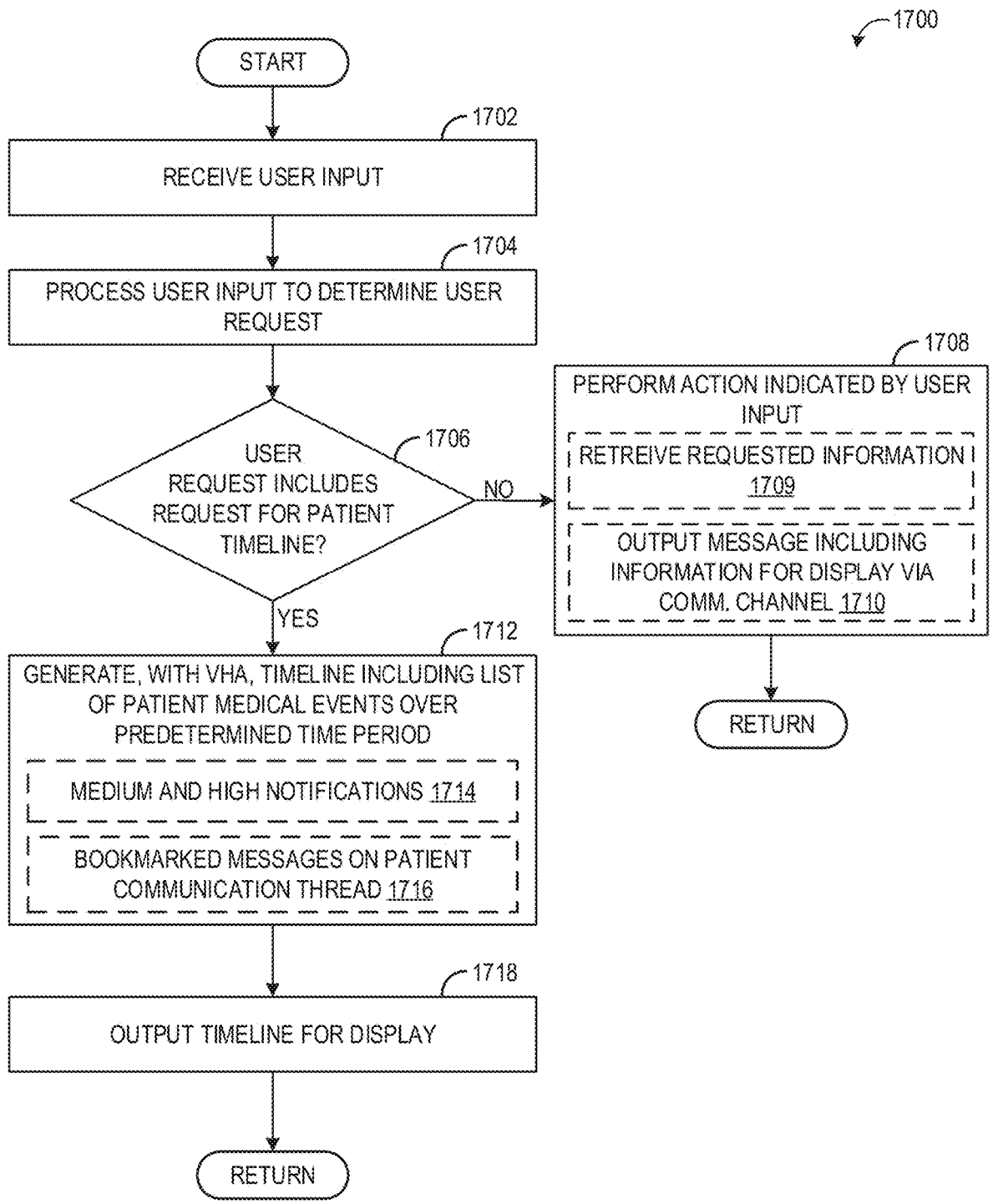
FIG. 17 is a flow chart illustrating an example method for generating and outputting a timeline via the collaborative healthcare system.

FIG. 16 is a flow chart illustrating a method 1600 for generating automatic notifications via a virtual healthcare assistant that are then output to one or more care providers. Method 1600 may be executed by a processor of a computing device (such as processor(s) 132 of server system 102 of FIG. 1) according to instructions stored on a non-transitory memory of the device (e.g., memory 130 shown in FIG. 1). Method 1600 is explained with respect to a specific patient (e.g., patient 1234), but it is to be understood that a similar method may be performed for each patient in the medical facility.

At 1602, method 1600 includes receiving patient monitoring data. The patient monitoring data may be received from the monitoring devices 120, digital twin 108, EMR database 122, and/or other suitable data source. The patient monitoring data may include any patient medical information, including but not limited to vital signs (e.g., blood pressure, heart rate, SpO2, temperature), diagnostic testing results, and/or other patient medical information. At 1604, the received patient monitoring data is compared to one or more predetermined thresholds to detect if a change in patient state has occurred. The predetermined thresholds may be set by a user (e.g., care provider), a virtual healthcare assistant, and/or a system administrator. The thresholds may be different for different patient medical parameters. For example, blood pressure may have different thresholds than heart rate. Further, more than one threshold may be assigned to a given patient medical parameter. For example, heart rate may have two thresholds, a first threshold that indicates a warning status of the patient, and a second (higher or lower) threshold that indicates a critical status of the patient. Further, different patients may have different thresholds for the same medical parameter. For example, a first patient may have a first threshold for heart rate that indicates the patient may be in a warning status, while a second patient may have a second threshold for heart rate that indicates the second patient is in the warning status.

At 1606, method 1600 determines if a threshold change in patient state is detected. For example, if a patient medical parameter (as determined from the monitoring data) meets a condition relative to a predetermined threshold for that medical parameter (e.g., if patient heart rate drops below the predetermined heart rate threshold), a threshold change in patient state is detected. The threshold change in patient state is used herein to differentiate significant changes in patient state, which may be medically relevant, from minor changes in patient state that may occur due to diurnal cycles, improving patient status, and so forth. Further, in some examples, a change in patient state may be detected based on more than one medical parameter. For example, a slight increase in patient temperature or a slight decrease in patient SpO2 may not individually indicate a change in patient state that warrants action, but if the slight increase in patient temperature is accompanied with the slight decrease in SpO2, a medically relevant, threshold change in patient state may be detected. If a threshold change in patient state is not detected, method 1600 returns to 1602 and continues to receive patient monitoring data. If a threshold change in patient state is detected, method 1600 proceeds to 1608 to automatically generate, with a VHA, a notification based on the detected change in patient state. In some examples, as indicated at 1610, the notification may include an alert of the change in patient state. For example, the notification may include information explaining the change in patient state (e.g., patient temperature has increased to 100.4° F.). Further, in some examples, as indicated at 1612, the notification may be classified according to the severity of the change in patient state. For example, if the patient medical parameter (e.g., heart rate) is below a first threshold but above a second threshold (e.g., below 50 but above 40), the notification indicating the change in patient state (e.g., change in heart rate) may be classified as a medium level notification, while if the patient medical parameter is below the second threshold, the notification may be classified as a high level notification.

At 1614, the notification is output for display on one or more suitable display devices. For example, as explained above with respect to FIGS. 8A-8C, the notification may be output as a pop-up notification on each display device of each care provider attending to the patient. The notification may be displayed on each display device regardless of what else (if anything) is currently being displayed on each display device. The notification may take on a particular form based on the classification level of the notification. For example, low level notifications may include portions in green (e.g., a banner or outline of the notification may be green), while a medium level notification may include portions in yellow and a high level notification may include portions in red.

Further, the notification may be preserved for future reference, as a banner in the communication thread for the patient, as indicated at 1616, and/or as a notification in a timeline for the patient, as indicated at 1618. For example, all medium and high level notifications may automatically be included in the patient's timeline. All notifications may be automatically inserted into the communication thread for that patient.

At 1620, method 1600 includes outputting for display an action menu including selectable control buttons, when requested by the user. The action menu may be associated with the notification and may be output for display in response to a user input (e.g., selecting the notification). The action menu may include buttons that, when selected, cause different actions to be performed, such as dismissing the notification, setting a snooze for the notification, or triggering display of additional patient information, such as triggering display of the communication thread for that patient. Accordingly, at 1622, method 1600 includes performing the action dictated by the selected control button when requested. For example, if the user selects the "go to patient" button from the action menu, the communication thread for that patient may be displayed. Method 1600 then returns.

While method 1600 was described above as being carried out by processor(s) 132 of server system 102 of FIG. 1 (as an example), it should be understood that at least some of the elements of method 1600 described above may be carried out by processor(s) 132 of server system 102 of FIG. 1 in concert with one or more care provider devices, such as care provider device 134 of FIG. 1. For example, when a notification is output for display (e.g., at 1614 of method 1600), the processor(s) 132 of server system 102 may output at least some of the notification to the care provider device 134, and the care provider device 134 may then process the received notification (e.g., insert the received notification into a notification template stored locally on care provider device) and display the notification. In another example, when the action menu is output for display (e.g., at 1620 of method 1600), the care provider device 134 may output the action menu for display on the care provider device, and then send a notification to the server system 102 of the user selection of a button of the action menu, if needed. For example, if the "go to patient" button is selected so that the communication thread for that patient is displayed on the care provider device, the server system 102 may send the communication thread to the care provider device, or send any messages from the communication thread that have yet to be viewed on the care provider device.

FIG. 17 is a flow chart illustrating a method 1700 for generating a timeline of relevant patient medical information, via a virtual healthcare assistant, that is then output to one or more care providers. Method 1700 may be executed by a processor of a computing device (such as processor(s) 132 of server system 102 of FIG. 1) according to instructions stored on a non-transitory memory of the device (e.g., memory 130 shown in FIG. 1). As explained above with respect to FIG. 1, the server system 102 may store/execute one or more virtual healthcare assistants (VHAs) that are configured to perform certain tasks related to providing medical information of the patient to the one or more care providers attending to the patient, as explained below.

At 1702, method 1700 includes receiving a natural language user input. The natural language user input may be input as a message from a care provider, via voice or text, and may include patient-specific information in natural language form. For example, as explained previously, each patient may have a dedicated communication channel including a communication thread that facilitates communication among the care providers treating the patient and one or more VHAs. When a care provider enters a natural language input on the communication thread, the input (e.g., message) may be received at the server system and the input may be processed, via the one or more VHAs, to determine the content of the natural language user input, as indicated at 1704. The one or more VHAs may utilize a speech recognition engine in examples where the natural user input is input via voice. As explained previously, the one or more VHAs may be trained to process natural language inputs to determine the content of the input, e.g., determine if the input includes a request for information, and if the content incudes a request for information, the one or more VHAs may be trained to determine which patient the care provider is referring to and what information is being requested. In some examples, each VHA may process a received message to understand (in natural language) the intent of the message and determine if the intent of the message includes a task that the VHA is trained/configured to perform. In some examples, the server system may include a central entity configured to understand the intent of the message (e.g., from the natural language of the message) and determine which VHA is best configured to handle the request. Then, the mapping from intent (and VHAs) to a specific API of a specific VHA is one-to-one, that is, only one VHA handles a specific intent (or intent-entity combination).

The information request may be an explicit request, where the care provider explicitly asks for certain medical information, such as "please send me the patient's heart rate over the last four hours." In other examples, the request may be implicit. Implicit requests may include assumptions (on the part of the VHAs executing on the server system) that certain medical information may be helpful, such as when a change in patient vital signs is detected, that are not accompanied by an actual request by the care provider.

At 1706, method 1700 determines if the user input includes a request for a patient timeline. A care provider may enter one or more natural language user inputs (e.g., messages on the communication thread) requesting to view a timeline, such as the timeline shown in FIG. 13. If the user input does not include a request a patient condition summary, for example if the user input includes a request for a single data set (e.g., just heart rate), a request for treatment guidelines or diagnosis guidelines, or if the user input is not directed at the VHA (e.g., the message is intended for another care provider), method 1700 proceeds to 1708 and performs one or more actions as indicated by the user input. For example, if the user input includes a request for a single piece of medical information from the patient's EMR, the VHA (e.g., EMR VHA) may retrieve the information from the patient's EMR and output the information as a message in the communication thread. Thus, in some examples, performing the one or more actions may include retrieving the requested information, as indicated at 1709, and outputting a message including the information for display via the communication channel, as indicated at 1710. In other examples, the one or more actions may simply include saving/distributing the message (e.g., when the user input does not include any requests for information).

If the user input does include a request for a patient timeline, method 1700 proceeds to 1712 to generate, with a VHA, a timeline including a list of patient medical events, including notifications and messages, over a predetermined time period. The timeline may include medium and high level notifications, as indicated at 1714. The timeline may further include bookmarked messages from the patient communication thread, as indicated at 1716. As explained above with respect to FIG. 12, select messages may be bookmarked by a user, which may then cause the bookmarked messages to be included in the timeline. The predetermined time period may be 8, 12, or 24 hours, or other suitable period of time.

At 1718, the timeline is output for display. For example, the timeline may be output on a display device of the user who requested to view the timeline. Method 1700 then returns.

While method 1700 was described above as being carried out by processor(s) 132 of server system 102 of FIG. 1 (as an example), it should be understood that at least some of the elements of method 1700 described above may be carried out by processor(s) 132 of server system 102 of FIG. 1 in concert with one or more care provider devices, such as care provider device 134 of FIG. 1. For example, the care provider device may receive the request to view the patient timeline, and may send a request for the most recent patient timeline to the server system 102. Further, the care provider device may receive the timeline (or aspects of the timeline) and may process the timeline and output the timeline for display on the display device of the care provider device. In still further examples, while method 1700 described the timeline as being generated in response to a user request to view the timeline, in some examples the timeline may be generated in an ongoing manner, e.g., the timeline may be updated each time a notification is generated and/or each time a message is bookmarked. Then, when requested, the generated timeline may be output for display. Furthermore, the timeline may be displayed in response to other types of user input, such as touch or mouse input selecting a timeline tab on a display.

The technical effect of generating communication channels including communication thread-dashboard pairs for each patient is to facilitate communication among care providers of the patient and allow virtual healthcare assistants to provide information retrieval and patient monitoring duties. By doing so, care provider work load may be reduced, communication among care providers may be increased to avoid redundant or missed care of the patient, and the communication occurring on the channel may be saved in a central location accessible by the care providers. By saving the communication on the channel, patient medical state, care decisions, and more may be viewable at a later time in context. The saved communication on the communication channel may be used to auto-populate medical records, reports, or other forms, and may be available for larger-scale (e.g., hospital-wide) analytics on treatment guidelines and patient outcomes. By generating and outputting notifications in a personalized and/or global manner, care providers may be provided with relevant patient medical information in a time-sensitive manner, which may enhance patient care and reduce redundant or unnecessary care provider actions. Further, by allowing a care provider to directly access relevant and/or curated patient medical information on demand from a notification or communication thread, unnecessary navigation through varying layers of menus to reach desired patient information may be reduced or avoided. Additionally, by providing a most recent and most relevant list of patient medical events (as determined by both the system and the care providers), handover between care providers may be made easier, further improving patient care.

In another representation, a system includes a display and a computing device operably coupled to the display and storing instructions executable to: output, to the display, a patient-specific communication thread including communication among one or more care providers monitoring a patient and a virtual healthcare assistant; responsive to a request to output a timeline for the patient, generate, with the virtual healthcare assistant, a list of medical events associated with the patient over a predetermined time period; and output, to the display, the list of patient medical parameters associated with the patient condition.

In another representation, a computing device comprises a display screen, the computing device being configured to display on the screen a communication thread, and additionally being configured to display on the screen a notification, wherein the communication thread displays communication between one or more care providers and a virtual healthcare assistant, the communication including medical information of a patient sent to the communication thread from the one or more care providers and/or the virtual healthcare assistant, wherein the notification is generated by the virtual healthcare assistant and displays time-sensitive and/or urgent medical information of the patient, and where the notification is displayable while the communication thread is in an unlaunched state and is selectable to launch the communication thread. The communication occurring on the communication thread further includes a representation of the notification.

An embodiment relates to a system including a display and a computing device operably coupled to the display and storing instructions executable to: output, to the display, a patient-specific communication thread including communication among one or more care providers monitoring a patient and a virtual healthcare assistant; generate, with the virtual healthcare assistant, a notification indicating a change in a state of the patient; and output, to the display, the notification, where the notification is displayable as part of the communication thread. In a first example of the system, the instructions are executable to receive patient monitoring data and generate the notification responsive to a parameter of the patient monitoring data reaching a predetermined threshold. In a second example of the system, which optionally includes the first example, the predetermined threshold is set by a user. In a third example of the system, which optionally includes one or both of the first and second examples, the instructions are executable to, upon outputting the notification and responsive to a user input selecting the notification, output, to the display, an action menu, the action menu including one or more control buttons. In a fourth example of the system, which optionally includes one or more or each of the first through third examples, the notification is displayed when the communication thread is in an unlaunched state, and wherein the instructions are executable to, responsive to receiving a user input selecting a first control button of the one or more control buttons, output to the display the communication thread including the notification displayed as a banner within the communication thread. In a fifth example of the system, which optionally includes one or more or each of the first through fourth examples, the notification is displayed as a banner within the communication thread, the banner inserted into the communication thread according to a time when the notification was generated. In a sixth example of the system, which optionally includes one or more or each of the first through fifth examples, the instructions are executable to output, to the display, a timeline including a list of medical events associated with the patient over a predetermined time period, the timeline output in response to a request from a user. In a seventh example of the system, which optionally includes one or more or each of the first through sixth examples, the notification is displayed in the timeline. In an eighth example of the system, which optionally includes one or more or each of the first through seventh examples, the instructions are executable to generate a reminder responsive to a request from a user, and output, to the display, the reminder at a time indicated by the user.

Another embodiment provides for a system including a display; and a computing device operably coupled to the display and storing instructions executable to: generate a plurality of patient-specific communication channels, wherein each channel comprises a patient-specific dashboard and a patient-specific communication thread; for a first communication channel of the plurality of patient-specific communication channels, store text- and/or rich media-based messages between one or more care providers monitoring a first patient and a virtual healthcare assistant on a first communication thread of the first communication channel, at least a portion of the messages on the first communication thread including medical data specific to the first patient; generate, with the virtual healthcare assistant, a first notification indicating a change in a state of the first patient; output, to the display, the first notification; and responsive to a user input associated with the first notification, output, to the display, the first communication thread. In a first example of the system, the instructions are executable to output the first notification to the display regardless of other display elements currently displayed on the display. In a second example of the system, which optionally includes the first example, the first notification is included in the first communication thread. In a third example of the system, which optionally includes one or both of the first and second examples, the instructions are executable to: for a second communication channel of the plurality of patient-specific communication channels, store text- and/or rich media-based messages between one or more care providers monitoring a second patient and the virtual healthcare assistant on a second communication thread of the second communication channel, at least a portion of the messages on the second communication thread including medical data specific to the second patient; generate, with the virtual healthcare assistant, a second notification indicating a change in a state of the second patient; output, to the display, the second notification; and responsive to a user input associated with the second notification, output, to the display, the second communication thread. In a fourth example of the system, which optionally includes one or more or each of the first through third examples, the display is a first display associated with a first care provider of the one or more care providers, wherein the user input is a first user input received via the first display, and further comprising a second display operably coupled to the computing device, the second display associated with second care provider of the one or more care providers. In a fifth example of the system, which optionally includes one or more or each of the first through fourth examples, the instructions are executable to: output, to the second display, the first notification; and responsive to a second user input associated with the first notification and received via the second display, output, to the second display, the first communication thread. In a sixth example of the system, which optionally includes one or more or each of the first through fifth examples, the instructions are executable to only output the first notification to the first display and not to the second display, and wherein the instructions are further executable to, responsive to a prompt, output the first communication thread to the second display.

An embodiment provides for a computing device comprising a display screen, the computing device being configured to display on the screen a communication thread, and additionally being configured to display on the screen a timeline, wherein the communication thread displays communication between one or more care providers and a virtual healthcare assistant, the communication including medical information of a patient sent to the communication thread from the one or more care providers and/or the virtual healthcare assistant, the communication further including one or more notifications of a state of the patient sent by the virtual healthcare assistant, the timeline including only a subset of the communication occurring on the communication thread over a predetermined time period. In a first example of the computing device, the communication on the communication thread includes a first message sent from the virtual healthcare assistant and a second message sent from the one or more care providers, and wherein the timeline includes only one of the first message and the second message. In a second example of the computing device, which optionally includes the first example, the timeline includes the one or more notifications. In a third example of the computing device, which optionally includes one or both of the first and second examples, the computing device is configured to display on the screen a representation of a first notification of the one or more notifications when the communication thread is in an unlaunched state, and responsive to a user input associated with the representation of the first notification, the computing device is configured to display on the screen the communication thread.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A system, comprising:
a computing device operably coupled to a display of a mobile device and storing instructions executable to:
output, to the display, a patient-specific communication thread including communication among one or more care providers monitoring a patient and a virtual healthcare assistant;

generate, with the virtual healthcare assistant, a notification indicating a change in a state of the patient;

output, to the display, the notification, where the notification is displayed when the communication thread is in an unlaunched state; and responsive to receiving a user input selecting the notification, output to the display the communication thread including the notification displayed as a banner within the communication thread in a position corresponding to when the notification was generated relative to when additional communication on the communication thread occurred, where the additional communication is viewable on the display by scrolling along a scrolling axis of the display that is parallel to a long axis of the display.

2. The system of claim 1, wherein the instructions are executable to receive patient monitoring data from one or more medical devices and generate the notification responsive to a parameter of the patient monitoring data reaching a predetermined threshold.

3. The system of claim 2, wherein the predetermined threshold is set by a user.

4. The system of claim 1, wherein the instructions are executable to, upon outputting the notification and responsive to the user input selecting the notification, output, to the display, an action menu, the action menu including one or more control buttons.

5. The system of claim 4, wherein the wherein the communication thread is output to the display responsive to a second user input selecting a first control button of the one or more control buttons.

6. The system of claim 1, wherein the instructions are executable to output, to the display, a timeline including a list of medical events associated with the patient over a predetermined time period, the timeline output in response to a request from a user.

7. The system of claim 6, wherein the notification is displayed in the timeline.

8. The system of claim 1, wherein the instructions are executable to generate a reminder responsive to a request from a user, and output, to the display, the reminder at a time indicated by the user.

9. A system, comprising:
a computing device operably coupled to a display of a mobile device and storing instructions executable to:
generate a plurality of patient-specific communication channels, wherein each channel comprises a patient-specific dashboard and a patient-specific communication thread;
for a first communication channel of the plurality of patient-specific communication channels, store text- and/or rich media-based messages between one or more care providers monitoring a first patient and a virtual healthcare assistant on a first communication thread of the first communication channel, at least a portion of the messages on the first communication thread including medical data specific to the first patient;
generate, with the virtual healthcare assistant, a first notification indicating a change in a state of the first patient, the change in the state of the first patient determined based on patient monitoring data received from one or more medical devices;
output, to the display, the first notification; and
responsive to a user input associated with the first notification, output, to the display, the first communication thread, where the first communication thread is launched from an unlaunched state in response to the user input.

10. The system of claim 9, wherein the instructions are executable to output the first notification to the display regardless of other display elements currently displayed on the display.

11. The system of claim 9, wherein the first notification is included in the first communication thread.

12. The system of claim 9, wherein the instructions are executable to:
for a second communication channel of the plurality of patient-specific communication channels, store text- and/or rich media-based messages between one or more care providers monitoring a second patient and the virtual healthcare assistant on a second communication thread of the second communication channel, at least a portion of the messages on the second communication thread including medical data specific to the second patient;
generate, with the virtual healthcare assistant, a second notification indicating a change in a state of the second patient;
output, to the display, the second notification; and
responsive to a user input associated with the second notification, output, to the display, the second communication thread.

13. The system of claim 9, wherein the display is a first display of a first mobile device associated with a first care provider of the one or more care providers, wherein the user input is a first user input received via the first display, further comprising a second display of a second mobile device operably coupled to the computing device, the second mobile device associated with second care provider of the one or more care providers.

14. The system of claim 13, wherein the instructions are executable to:
output, to the second display, the first notification; and
responsive to a second user input associated with the first notification and received via the second display, output, to the second display, the first communication thread.

15. The system of claim 13, wherein the instructions are executable to only output the first notification to the first display and not to the second display, and wherein the instructions are further executable to, responsive to a prompt, output the first communication thread to the second display.

16. A mobile computing device comprising a display screen, the computing device being configured to display on the screen a communication thread, the communication thread launched from an unlaunched state in response to a user input, and the computing device additionally being configured to display on the screen a timeline, wherein the communication thread displays communication between one or more care providers and a virtual healthcare assistant, the communication including medical information of a patient sent to the communication thread from the one or more care providers and/or the virtual healthcare assistant, the communication further including one or more notifications of a state of the patient sent by the virtual healthcare assistant, where the one or more notifications are each positioned within the communication thread at a time corresponding to when the one or more notification were generated relative to other communication on the communication thread and the additional communication is viewable via scrolling along a scroll axis of the screen, and the user input that launches the communication thread is a user input to the one or more notifications, the timeline including only a subset of the communication occurring on the communication thread over a predetermined time period, the subset of the communication including only messages bookmarked via user input by a care provider of the one or more care providers.

17. The computing device of claim 16, wherein the communication on the communication thread includes a first message sent from the virtual healthcare assistant and a second message sent from the one or more care providers, and wherein the timeline includes only one of the first message and the second message.

18. The computing device of claim 17, wherein the timeline includes the one or more notifications.

19. The computing device of claim 16, wherein the computing device is configured to display on the screen a representation of a first notification of the one or more notifications when the communication thread is in the unlaunched state, and wherein the user input is a selection of the representation of the first notification.

\* \* \* \* \*